United States Patent
Francis et al.

(10) Patent No.: US 10,406,229 B2
(45) Date of Patent: Sep. 10, 2019

(54) METHODS AND COMPOSITIONS RELATED TO INHIBITION OF VIRAL ENTRY

(71) Applicant: UNIVERSITY OF UTAH RESEARCH FOUNDATION, Salt Lake City, UT (US)

(72) Inventors: J. Nicholas Francis, Salt Lake City, UT (US); Joseph S. Redman, Salt Lake City, UT (US); Michael S. Kay, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/448,492

(22) Filed: Mar. 2, 2017

(65) Prior Publication Data

US 2017/0239364 A1    Aug. 24, 2017

Related U.S. Application Data

(62) Division of application No. 14/007,785, filed as application No. PCT/US2012/031015 on Mar. 28, 2012, now abandoned.

(60) Provisional application No. 61/468,094, filed on Mar. 28, 2011.

(51) Int. Cl.

| | |
|---|---|
| C07K 7/08 | (2006.01) |
| A61K 38/10 | (2006.01) |
| C07J 41/00 | (2006.01) |
| A61K 45/06 | (2006.01) |
| C07K 7/06 | (2006.01) |
| A61K 38/08 | (2019.01) |
| A61K 47/60 | (2017.01) |
| A61K 47/54 | (2017.01) |
| A61K 47/64 | (2017.01) |

(52) U.S. Cl.
CPC .............. *A61K 45/06* (2013.01); *A61K 38/08* (2013.01); *A61K 47/542* (2017.08); *A61K 47/554* (2017.08); *A61K 47/60* (2017.08); *A61K 47/643* (2017.08); *C07K 7/06* (2013.01); *C07K 7/08* (2013.01)

(58) Field of Classification Search
None
See application file for complete search history.

(56) References Cited

U.S. PATENT DOCUMENTS

| | | |
|---|---|---|
| 6,506,554 B1 | 1/2003 | Chan et al. |
| 6,818,740 B1 | 11/2004 | Eckert et al. |
| 6,841,657 B2 | 1/2005 | Eckert et al. |
| 7,129,227 B1 | 10/2006 | Kucera et al. |
| 9,381,226 B2 | 7/2016 | Kay et al. |
| 2011/0027183 A1 | 2/2011 | Mier et al. |
| 2016/0354428 A1 | 12/2016 | Kay et al. |

FOREIGN PATENT DOCUMENTS

| | | | |
|---|---|---|---|
| WO | 2005/018666 A1 | | 3/2005 |
| WO | 2005/080418 A2 | | 9/2005 |
| WO | 2008/098182 A1 | | 8/2008 |
| WO | WO2008-098182 | * | 8/2008 |
| WO | 2009/092612 A1 | | 7/2009 |

OTHER PUBLICATIONS

Huet et al. (Long-Lasting Enfuvirtide Carrier Pentasaccharide Conjugates with Potent Anti-Human Immunodeficiency Virus Type 1 Activity, Antimicrobial Agents and Chemotherapy; 2010 p. 134-142).*

Ingallinella et al. (Addition of a cholesterol group to an HIV-1 peptide fusion inhibitor dramatically increases its antiviral potency; PNAS, Apr. 7, 2009; vol. 106, No. 14, 5801-5806).*

Bianchi et al., "Covalent stabilization of coiled coils of the HIV gp41 N region yields extremely potent and broad inhibitors of viral infection," *Proceedings of the National Academy of Sciences of the United States of America* 102(36):12903-12908, 2005.

Brünger et al., "Crystallography & NMR System: A New Software Suite for Macromolecular Structure Determination," *Acta Crystallographica* D54(5):905-921, 1998.

Chan et al., "Core Structure of gp41 from the HIV Envelope Glycoprotein," *Cell* 89(2):263-273, 1997.

Chan et al., "Evidence that a prominent cavity in the coiled coil of HIV type 1 gp41 is an attractive drug target," *Proceedings of the National Academy of Sciences of the United States of America* 95(26):15613-15617, 1998.

Chan et al., "HIV Entry and Its Inhibition," *Cell* 93(5):681-684, 1998.

Cheng et al., "Enhanced Hepatic Uptake and Bioactivity of Type α1(I) Collagen Gene Promoter-Specific Triplex-Forming Oligonucleotides after Conjugation with Cholesterol," *Journal of Pharmacology and Experimental Therapeutics* 317(2):797-805, 2006.

Chong et al., "Comparative immunological properties of enantiomeric peptides," *Letters in Peptide Science* 3(2):99-106, 1996.

Choudhry et al., "Increased Efficacy of HIV-1 Neutralization by Antibodies at Low CCR5 Surface Concentration," *Biochemical and Biophysical Research Communications* 348(3):1107-1115, 2006. (16 pages).

Cole et al., "Thermodynamics of Peptide Inhibitor Binding to HIV-1 gp41," *Biochemistry* 40(19):5633-5641, 2001.

Collaborative Computational Project, No. 4, "The CCP4 Suite: Programs for Protein Crystallography," *Acta Crystallographica* D50(5): 760-763, 1994. (5 pages).

Debnath et al., "Structure-Based Identification of Small Molecule Antiviral Compounds Targeted to the gp41 Core Structure of the Human Immunodeficiency Virus Type 1," *Journal of Medicinal Chemistry* 42(17):3203-3209, 1999.

Eckert et al., "Design of potent inhibitors of HIV-1 entry from the gp41 N-peptide region," *Proceedings of the National Academy of Sciences of the United States of America* 98(20):11187-11192, 2001.

(Continued)

*Primary Examiner* — James H Alstrum-Acevedo
*Assistant Examiner* — Tara L Martinez
(74) *Attorney, Agent, or Firm* — Seed Intellectual Property Law Group LLP

(57) ABSTRACT

Disclosed herein are compositions and methods for inhibiting viral entry.

18 Claims, 5 Drawing Sheets

Specification includes a Sequence Listing.

(56) References Cited

OTHER PUBLICATIONS

Eckert et al., "Inhibiting HIV-1 Entry: Discovery of D-Peptide Inhibitors that Target the gp41 Coiled-Coil Pocket," *Cell* 99(1):103-115, 1999.

Eckert et al., "Mechanisms of Viral Membrane Fusion and Its Inhibition," *Annual Review of Biochemistry* 70:777-810, 2001. (36 pages).

Emsley et al., "Coot: model-building tools for molecular graphics," *Acta Crystallographica* D60(12):2126-2132, 2004.

Ernst et al., "Design of a Protein Surface Antagonist Based on α-Helix Mimicry: Inhibition of gp41 Assembly and Viral Fusion," *Angewandte Chemie International Edition* 41(2):278-281, 2002.

Extended European Search Report, dated Apr. 23, 2010, for European Application No. 08729413, 14 pages.

Extended European Search Report, dated Apr. 23, 2013, for European Application No. 13156450, 9 pages.

Extended European Search Report, dated Nov. 4, 2014, for European Application No. 12763412, 8 pages.

Ferrer et al., "Selection of gp41-mediated HIV-1 cell entry inhibitors from biased combinatorial libraries of non-natural binding elements," *Nature Structural Biology* 6(10):953-960, 1999.

Final Office Action, dated Dec. 19, 2013, for U.S. Appl. No. 12/526,071, Kay et al., "Methods and Compositions Related to Inhibition of Viral Entry," 5 pages.

Final Office Action, dated Jan. 29, 2016, for U.S. Appl. No. 14/007,785, Francis et al., "Methods and Compositions Related to Inhibition of Viral Entry," 15 pages.

Final Office Action, dated Oct. 28, 2015, for U.S. Appl. No. 12/526,071, Kay et al., "Methods and Compositions Related to Inhibition of Viral Entry," 7 pages.

Francis et al., "Design of a modular tetrameric scaffold for the synthesis of membrane-localized D-peptide inhibitors of HIV-1 entry," *Bioconjugate Chemistry* 23(6):1252-1258, 2012. (15 pages).

Frey et al., "Small molecules that bind the inner core of gp41 and inhibit HIV envelope-mediated fusion," *Proceedings of the National Academy of Sciences of the United States of America* 103(38):13938-13943, 2006.

Furuta et al., "Capture of an early fission-active conformation of HIV-1 gp41," *Nature Structural Biology* 5(4):276-279, 1998. (5 pages).

Hamburger et al., "Steric Accessibility of the HIV-1 gp41 N-trimer Region," *The Journal of Biological Chemistry* 280(13):12567-12572, 2005. (7 pages).

Harris et al "Effect of Pegylation on Pharmaceuticals," *Nature Reviews Drug Discovery* 2(3):214-221, 2003.

Huet et al., "Long-Lasting Enfuvirtide Carrier Pentasaccaride Conjugates with Potent Anti-Human Immunodeficiency Virus Type 1 Activity," *Antimicrobial Agents and Chemotherapy* 54(1):134-142, 2010.

Ingallinella et al., "Addition of a cholesterol group to an HIV-1 peptide fusion inhibitor dramatically increases its antiviral potency," *Proceedings of the National Academy of Sciences of the United States of America* 106(14):5801-5806, 2009.

International Preliminary Report on Patentability, dated Aug. 11, 2009, for International Application No. PCT/US2008/053447, 4 pages.

International Preliminary Report on Patentability, dated Oct. 1, 2013, for International Application No. PCT/US2012/031015, 9 pages.

International Search Report and Written Opinion, dated Aug. 10, 2012, for International Application No. PCT/US2012/031015, 14 pages.

International Search Report and Written Opinion, dated May 8, 2008, for International Application No. PCT/US2008/053447, 5 pages.

Jiang et al., "HIV-1 inhibition by a peptide," *Nature* 365(6442):113, 1993.

Jiang et al., "N-Substituted Pyrrole Derivatives as Novel Human Immunodeficiency Virus Type 1 Entry Inhibitors That Interfere with the gp41 Six-Helix Bundle Formation and Block Virus Fusion," *Antimicrobial Agents and Chemotherapy* 48(11):4349-4359, 2004. (12 pages).

Jin et al., "Design of a Peptide Inhibitor that Blocks the Cell Fusion Mediated by Glycoprotein 41 of Human Immunodeficiency Virus Type 1," *AIDS Research and Human Retroviruses* 16(17):1797-1804, 2000.

Judice et al., "Inhibition of HIV type 1 infectivity by constrained α-helical peptides: Implications for the viral fusion mechanism," *Proceedings of the National Academy of Sciences of the United States of America* 94(25):13426-13430, 1997.

Louis et al., "Covalent Trimers of the Internal N-terminal Trimeric Coiled-coil of gp41 and Antibodies Directed against Them Are Potent Inhibitors of HIV Envelope-mediated Cell Fusion," *The Journal of Biological Chemistry* 278(22):20278-20285, 2003.

Lu et al., "A trimeric structural domain of the HIV-1 transmembrane glycoprotein," *Nature Structural Biology* 2(12):1075-1082, 1995.

McCoy et al., "Likelihood-enhanced fast translation functions," *Acta Crystallographica* D61(4):458-464, 2005.

Miller et al., "A human monoclonal antibody neutralizes diverse HIV-1 isolates by binding a critical gp41 epitope," *Proceedings of the National Academy of Sciences of the United States of America* 102(41):14759-14764, 2005.

Milton et al., "Total Chemical Synthesis of a D-Enzyme: The Enantiomers of HIV-1 Protease Show Demonstration of Reciprocal Chiral Substrate Specificity," *Science* 256(5062):1445-1448, 1992.

Noren et al., "Construction of High-Complexity Combinatorial Phage Display Peptide Libraries," *Methods* 23(2):169-178, 2001.

Office Action, dated Apr. 28, 2014, for Canadian Application No. 2,677,665, 6 pages.

Office Action, dated Feb. 24, 2011, for European Application No. 08729413, 6 pages.

Office Action, dated Jan. 30, 2014, for European Application No. 13156450, 5 pages.

Office Action, dated Jul. 19, 2016, for European Application No. 12763412, 4 pages.

Office Action, dated Jun. 2, 2015, for Canadian Application No. 2,677,665, 4 pages.

Office Action, dated Mar. 15, 2016, for Japanese Application No. 2014-502764, 5 pages. (English Translation).

Office Action, dated Mar. 30, 2015, for European Application No. 13156450, 5 pages.

Office Action, dated May 26, 2016, for Canadian Application No. 2,677,665, 3 pages.

Office Action, dated Oct. 25, 2016, for Japanese Application No. 2014-502764, 3 pages. (English Translation).

Office Action, dated Sep. 1, 2015, for European Application No. 12763412, 5 pages.

Office Action, dated Feb. 27, 2013, for U.S. Appl. No. 12/526,071, Kay et al., "Methods and Compositions Related to Inhibition of Viral Entry," 6 pages.

Office Action, dated Jun. 22, 2015, for U.S. Appl. No. 14/007,785, Francis et al., "Methods and Compositions Related to Inhibition of Viral Entry," 14 pages.

Office Action, dated Mar. 2, 2015, for U.S. Appl. No. 12/526,071, Kay et al., "Methods and Compositions Related to Inhibition of Viral Entry," 6 pages.

Office Action, dated Sep. 2, 2016, for U.S. Appl. No. 14/007,785, Francis et al., "Methods and Compositions Related to Inhibition of Viral Entry," 18 pages.

Otwinowski et al., "Processing of X-Ray Diffraction Data Collected in Oscillation Mode," *Methods in Enzymology* 276:307-326, 1997.

Pappenheimer et al., "Absorption and Excretion of Undegradable Peptides: Role of Lipid Solubility and Net Charge," *The Journal of Pharmacology and Experimental Therapeutics* 280(1):292-300, 1997.

Pappenheimer et al., "Intestinal absorption and excretion of octapeptides composed of D amino acids," *Proceedings of the National Academy of Sciences of the United States of America* 91(5):1942-1945, 1994.

Platt et al., "Kinetic Factors Control Efficiencies of Cell Entry, Efficacies of Entry Inhibitors, and Mechanisms of Adaptation of Human Immunodeficiency Virus," *Journal of Virology* 79(7):4347-4356, 2005. (11 pages).

(56) References Cited

OTHER PUBLICATIONS

Requirement for Restriction/Election, dated Apr. 27, 2012, for U.S. Appl. No. 12/526,071, Kay et al., "Methods and Compositions Related to Inhibition of Viral Entry," 9 pages.
Requirement for Restriction/Election, dated Mar. 28, 2017, for U.S. Appl. No. 15/171,753, Kay et al., "Methods and Compositions Related to Inhibition of Viral Entry," 6 pages.
Requirement for Restriction/Election, dated Oct. 23, 2014, for U.S. Appl. No. 14/007,785, Francis et al., "Methods and Compositions Related to Inhibition of Viral Entry," 10 pages.
Rimsky et al., "Determinants of Human Immunodeficiency Virus Type 1 Resistance to gp41-Derived Inhibitory Peptides," *Journal of Virology* 72(2):986-993, 1998.
Root et al., "Protein Design of an HIV-1 Entry Inhibitor," *Science* 291(5505):884-888, 2001.
Root et al., "HIV-1 gp41 as a Target for Viral Entry Inhibition," *Current Pharmaceutical Design* 10(15): 1805-1825, 2004. (22 pages).
Sadowski et al., "A Synthetic Peptide Blocking the Apolipoprotein E/β-Amyloid Binding Mitigates β-Amyloid Toxicity and Fibril Formation in Vitro and Reduces β-Amyloid Plaques in Transgenic Mice," *American Journal of Pathology* 165(3):937-948, 2004.
Schumacher et al., "Identification of D-Peptide Ligands Through Mirror-Image Phage Display," *Science* 271(5257):1854-1857, 1996.
Scott et al., "Phage-display Vectors," in *Phage Display: A Laboratory Manual*, Cold Springs Harbor Laboratory Press, New York City, New York, USA, 2001, pp. 2.1-2.19. (20 pages).
Sia et al., "Short constrained peptides that inhibit HIV-1 entry," *Proceedings of the National Academy of Sciences of the United States of America* 99(23): 14664-14669, 2002.
Sidhu et al., "Phage Display for Selection of Novel Binding Peptides," *Methods in Enzymology* 328:333-363, 2000. (32 pages).
Steger et al., "Kinetic Dependence to HIV-1 Entry Inhibition," *The Journal of Biological Chemistry* 281(35):25813-25821, 2006. (10 pages).
Stephens et al., "Inhibiting HIV Fusion with a β-Peptide Foldamer," *Journal of the American Chemical Society* 127(38): 13126-13127, 2005. (6 pages).
Tan et al., "Atomic structure of a thermostable subdomain of HIV-1 gp41," *Proceedings of the National Academy of Sciences of the United States of America* 94(23):12303-12308, 1997.
Wei et al., "Emergence of Resistant Human Immunodeficiency Virus Type 1 in Patients Receiving Fusion Inhibitor (T-20) Monotherapy," *Antimicrobial Agents and Chemotherapy* 46(6):1896-1905, 2002. (11 pages).
Weissenhorn et al., "Atomic structure of the ectodomain from HIV-1 gp41," *Nature* 387(6631):426-430, 1997.
Welch et al., "Design of a Potent D-Peptide HIV-1 Entry Inhibitor with a Strong Barrier to Resistance," *Journal of Virology* 84(21):11235-11244, 2010. (11 pages).
Welch et al., "Potent D-peptide inhibitors of HIV-1 entry," *Proceedings of the National Academy of Sciences of the United States of America* 104(43):16828-16833, 2007.
Wild et al., "A synthetic peptide inhibitor of human immunodeficiency virus replication: Correlation between solution structure and viral inhibition," *Proceedings of the National Academy of Sciences of the United States of America* 89(21):10537-10541, 1992.
Wild et al., "Peptides corresponding to a predictive α-helical domain of human immunodeficiency virus type 1 gp41 are potent inhibitors of virus infection," *Proceedings of the National Academy of Sciences of the United States of America* 91(21):9770-9774, 1994.

Zhang et al., "Multiple-Peptide Conjugates for Binding β-Amyloid Plaques of Alzheimer's Disease," *Bioconjugate Chemistry* 14(1):86-92, 2003.
Zhao et al., "XTT Formazan Widely Used to Detect Cell Viability Inhibits HIV Type 1 Infection in Vitro by Targeting gp41," *AIDS Research and Human Retroviruses* 18(14):989-997.
Final Office Action, dated Oct. 18, 2018, for U.S. Appl. No. 15/171,753, Kay et al., "Methods and Compositions Related to Inhibition of Viral Entry," 13 pages.
Gait et al., "Progress in anti-HIV structure-based drug design," *Trends in Biotechnology* 13(10):430-438, 1995.
Gali et al., "In Vitro Evaluation of Viability, Integrity, and Inflammation in Genital Epithelia upon Exposure to Pharmaceutical Excipients and Candidate Microbicides," *Antimicrobial Agents and Chemotherapy* 54 (12):5105-5114, 2010.
Gallo et al., "The Stability of the Intact Envelope Glycoproteins Is a Major Determinant of Sensitivity of HIV/SIV to Peptidic Fusion Inhibitors," *Journal of Molecular Biology* 340(1):9-14, 2004.
Naider et al., "Peptides in the treatment of AIDS," *Current Opinion in Structural Biology* 19(4):473-482, 2009.
Office Action, dated Apr. 19, 2018, for Canadian Application No. 2,677,665, 3 pages.
Office Action, dated Mar. 12, 2018, for Canadian Application No. 2,868,735, 6 pages.
Office Action, dated May 4, 2017, for Canadian Application No. 2,677,665, 3 pages.
Office Action, dated Oct. 12, 2018, for Canadian Application No. 2,868,735, 4 pages.
Office Action, dated Dec. 28, 2017, for U.S. Appl. No. 15/171,753, Kay et al., "Methods and Compositions Related to Inhibition of Viral Entry," 8 pages.
Denton et al., "One Percent Tenofovir Applied Topically to Humanized BLT Mice and Used According to the CAPRISA 004 Experimental Design Demonstrates Partial Protection from Vaginal HIV Infection, Validating the BLT Model for Evaluation of New Microbicide Candidates," *Journal of Virology* 85(15):7582-7593, 2011.
Eckert et al., "Characterization of the steric defense of the HIV-1 gp41 N-trimer region," *Protein Sci.* 17(12):2091-2100, 2008.
Francis et al., "Preclinical Characterization of a Potent D-Peptide Inhibitor of HIV Entry: Cholesterol-conjugated PIE12-trimer," *HIV Research for Prevention Conference*, Chicago, Illinois, Oct. 17-21, 2016. (1 page).
Kay, "Design and Preclinical Characterization of a D-Peptide HIV Entry Inhibitor," *HIV Research .For Prevention Conference*, Chicago, Illinois, Oct. 17-21, 2016. (4 pages).
Kim et al., "Peptide Mimic of the HIV Envelope gp120-gp41 Interface," *Journal of Molecular Biology* 376(3):786-797, 2008.
Kol et al., "A Stiffness Switch in Human Immunodeficiency Virus," *Biophys. J* 92:1777-1783, 2007.
Kol et al., "The effect of purification method on the completeness of the immature HIV-1 Gag shell,"*J. Virol. Methods* 169:244-247, 2010.
Pang et al., "Virion stiffness regulates immature HIV-1 entry," *Retrovirology* 10:4, 2013. (11 pages).
Weinstock et al., "Protease-Resistant Peptide Design—Empowering Nature's Fragile Warriors Against HIV," *Biopolymers* 98(5):431-442, 2012.
Welch et al., "Discovery and Design of Potent D-Peptide Inhibitors of HIV-1 Entry," *West Coast Retrovirus Meeting*, Palm Springs, California, Oct., 2007. (20 pages).

\* cited by examiner a b

METHODS AND COMPOSITIONS RELATED TO INHIBITION OF VIRAL ENTRY

CROSS REFERENCE TO RELATED APPLICATIONS

This application is a divisional application of U.S. patent application Ser. No. 14/007,785, filed Feb. 13, 2014; which is a U.S. National Stage Application under 35 U.S.C. 371 of International Application No. PCT/US2012/031015, with an international filing date of Mar. 28, 2012, which claims the benefit of U.S. Provisional Application No. 61/468,094 filed Mar. 28, 2011. The aforementioned applications are herein incorporated by reference in their entirety.

STATEMENT REGARDING FEDERALLY SPONSORED RESEARCH

This invention was made with government support under Grant Number AI R01 076168, awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690181_402D1 SEQUENCE_LISTING.txt. The text file is 9.3 KB, was created on May 14, 2018, and is being submitted electronically via EFS-Web.

BACKGROUND

HIV entry is mediated by the viral envelope glycoprotein, which comprises non-covalently associated surface (gp120) and transmembrane (gp41) subunits. gp120 is primarily involved in recognition of cellular receptors, while gp41 directly mediates membrane fusion. When peptides isolated from the gp41 N- and C-peptide regions (N- and C-peptides) are mixed in solution, they form a six-helix bundle, which represents the post-fusion gp41 structure. Three N-peptides form a central parallel trimeric coiled coil (N-trimer) surrounded by three antiparallel helical C-peptides that nestle into long grooves between neighboring N-peptides. The importance of this structure is indicated by the dominant negative inhibition of HIV entry by N- and C-peptides.

The available inhibitory and structural data support a working model of HIV membrane fusion (FIG. 1). Initially, gp120 interacts with cellular CD4 and a chemokine coreceptor (typically CXCR4 or CCR5), causing large conformational changes in gp120 that propagate to gp41 via the gp41-gp120 interface. gp41 then undergoes a structural rearrangement that unleashes its N-terminal fusion peptide, which embeds in the target cell membrane. At this stage of fusion, gp41 adopts an extended "prehairpin intermediate" conformation that bridges both viral and cellular membranes and exposes the N-trimer region. This intermediate is relatively long-lived (minutes), but ultimately collapses as the N- and C-peptide regions of each gp41 monomer associate to form a hairpin structure. Three such hairpins (trimer-of-hairpins) form the 6-helix bundle, which forces the viral and cellular membranes into tight apposition and leads to membrane fusion. This structure likely corresponds to the core of the fusion-active state of gp41 and shows similarity to the proposed fusogenic structures of envelope fusion proteins from influenza, Moloney Murine Leukemia Virus, and simian immunodeficiency virus (SIV), and Ebola virus.

According to this model, an inhibitor that binds to the N-trimer and prevents hairpin formation can inhibit viral entry. This has been well supported by the discovery of numerous peptide, protein, and small molecule inhibitors that bind the N-trimer. A particularly interesting feature of the N-trimer is the deep hydrophobic "pocket" formed by its 17 C-terminal residues. This pocket has several enticing features as an inhibitory target including: (1) a very highly conserved sequence, (2) an essential role in viral entry, (3) a compact binding site vulnerable to inhibition by short peptides, and (4) the availability of several designed peptides (e.g., IQN17, IZN17, 5-helix, $N_{CCG}N13$ that authentically mimic the pocket structure). What is needed in the art are peptides with suitable pharmacokinetic properties that can inhibit the entry of gp41 into cells.

BRIEF DESCRIPTION OF THE DRAWINGS

The accompanying drawings, which are incorporated in and constitute a part of this specification, together with the description, illustrate certain embodiments of the disclosed compositions and methods.

DETAILED DESCRIPTION

Figure 1:
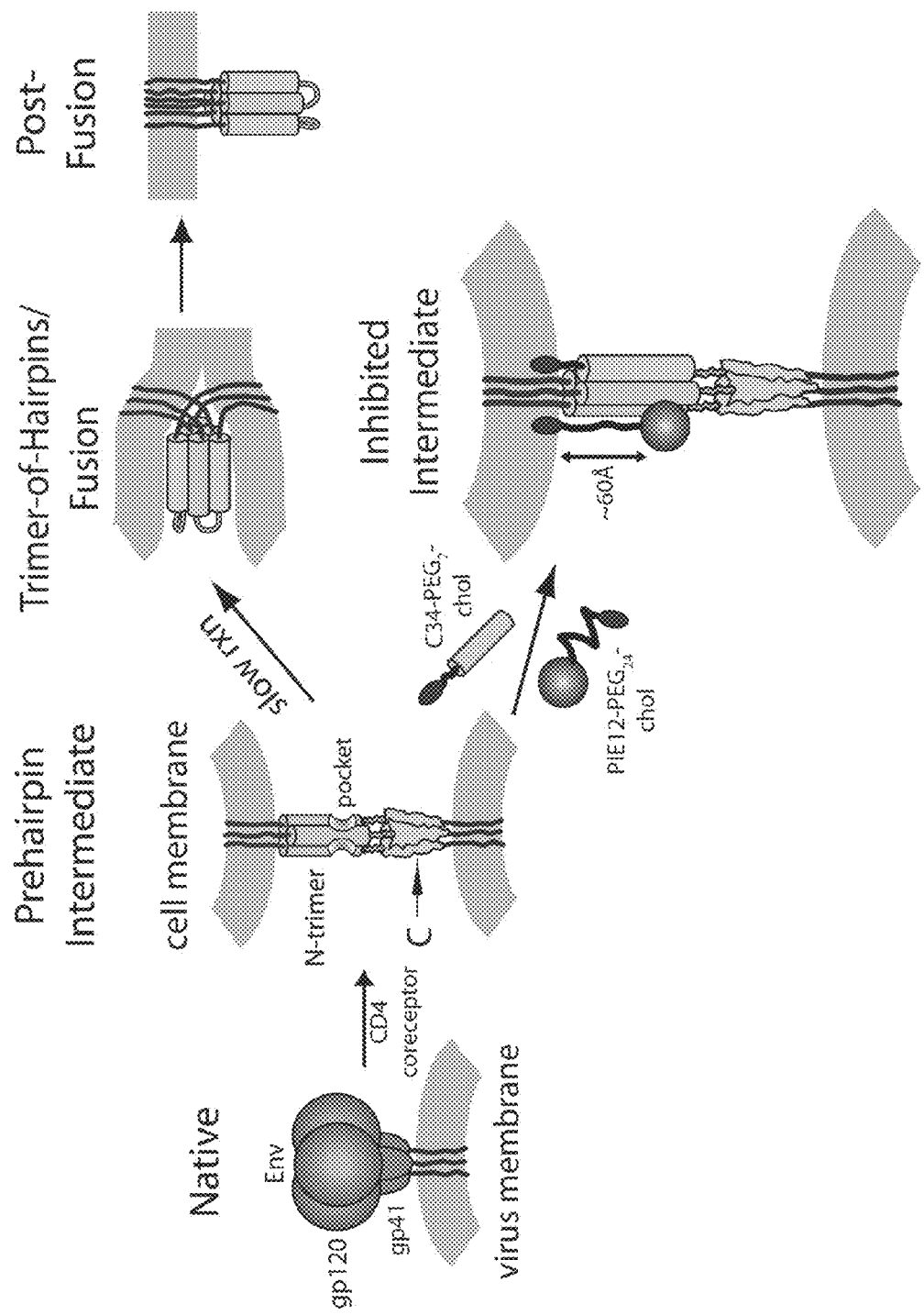
FIG. 1 shows an embodiment of a HIV entry pathway. The gp41 fusion peptide and transmembrane domain are also shown. For clarity, gp120 is omitted from the prehairpin intermediate.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a polypeptide is disclosed and discussed and a number of modifications that can be made to a number of molecules including the polypeptide are discussed, each and every combination and permutation of polypeptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Definitions

Unless defined otherwise, all technical and scientific terms used herein have the meanings that would be commonly understood by one of skill in the art in the context of the present specification.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein.

Synthetic C-peptides (peptides corresponding to the C-helix), such as DP178 and C34, are potent inhibitors of HIV-1 membrane fusion and are effective against both laboratory-adapted strains and primary isolates. Based on the structural features of the gp41 core, these peptides are thought to act through a dominant-negative mechanism, in which exogenous C-peptides bind to the central coiled-coil of gp41 and lead to its inactivation. These peptides likely act on a pre-hairpin intermediate of gp41 that forms when the native gp41 structure (i.e., the nonfusogenic conformation present on free virions) is perturbed by gp120/CD4/coreceptor interactions. This pre-hairpin intermediate has an exposed N-coiled-coil, thereby allowing C-peptides to bind and inactivate gp41 prior to the formation of the fusion-active hairpin structure. Therefore, compounds that bind with high affinity to this cavity and prevent normal N- and C-helix pairing are effective HIV-1 inhibitors. In addition, residues in the cavity are highly conserved among diverse HIV-1 isolates. Because of the high structural conservation, drugs targeting this site would have broad activity against diverse HIV isolates.

As described herein, the pocket on the surface of the N-helix coiled-coil of HIV-1 envelope protein gp41 subunit is a drug target. Similarly, cavities on other pathogens (e.g., HIV-2) which can cause AIDS or on pathogens which cause AIDS-like conditions in nonhuman mammals (e.g., SIV) are also drug targets. Available methods (e.g., mirror image phage display methods, combinational chemistry, computational approaches and other drug screening and medicinal chemistry methods) can be used to identify peptides, D-peptides, including multimers, and peptidomimetics and small molecules that bind the coiled-coil cavity of HIV-1 (and/or HIV-2) with sufficient affinity to interfere with viral entry into cells and, thus, inhibit viral infection. Mirror image phage display has been used to identify D-peptides which bind to a cavity on the surface of the N-helix coiled-coil of HIV-1 gp41.

Disclosed herein are compositions comprising D-peptides which interact with the N-trimer pocket of a viral transmembrane protein. For example, the D-peptides can bind to a cavity on the surface of the N-helix coiled-coil of HIV envelope glycoprotein gp41 (e.g., HIV-1, HIV-2). Such D-peptides can be of any length, provided that they are of sufficient length to bind the cavity in such a manner that they interfere with the interaction of the N-helix coiled-coil cavity and amino acid residues of the C-peptide region of viral gp41 and prevent, or inhibit, viral entry into the cells. For example, the peptide can comprise at least 2, 3, 4, 5, 6, 7, 8, 9, or 10 core amino acid residues in length. The amino acid residues can be naturally occurring or non-naturally occurring or modified, as described herein. Examples of peptides that bind the N-trimer of HIV gp41 may be found in U.S. application Ser. No. 12/526,071, which is incorporated in its entirety by reference herein, and as shown in Table 1.

D-peptides are peptides which are of the opposite handedness from the handedness of naturally-occurring peptides. Consequently, D-peptides do not serve as efficient substrates for enzymes, and, therefore, are not as readily degraded as L-peptides. In addition, there is no known effective immune response which targets D-peptides and therefore, they do not elicit an immune response comparable to that elicited by L amino acid peptides. Furthermore, D-peptides have several potential advantages over L-peptide including: (1) D-peptides are resistant to proteases, a property that can dramatically increase serum half-life, (2) L-peptides must be injected to avoid digestion, but short D-peptides can be absorbed systemically when taken orally, and (3) D-peptides represent a rich source of structural diversity because they can bind to targets with unique interface geometries not available to L-peptides.

Examples of D-peptides, identified as described herein, are shown below. In certain embodiments, D-peptides are referred to as Pocket-specific Inhibitors of Entry (PIE). An example of such a D-peptide inhibitor is PIE7, which is represented by the sequence Ac-KGACDYPEWQWLCAA-NH2 (SEQ ID NO: 6). In certain embodiments, one or more N-terminal lysine residues may be added to a D-peptide to improve water solubility. Particular embodiments of the D-peptides disclosed herein may be shown with the linker sequence "PEG" before the amino acid sequence.

Disclosed in Table 1 are various examples of D-peptides that can be used with the methods and compositions disclosed herein:

TABLE 1

D-peptide binding and neutralization

| Sample | Sequence |
|---|---|
| D10-p5 | KKGACELLGWEWAWLCAA (SEQ ID NO: 1) |
| 2K-PIE1 | KKGACESPEWRWLCAA (SEQ ID NO: 2) |
| 2K-PIE2 | KKGACDYPEWRWLCAA (SEQ ID NO: 3) |
| PIE2-AAA | KGACDYPEWRWLCAAA (SEQ ID NO: 4) |
| PIE2 | KGACDYPEWRWLCAA (SEQ ID NO: 5) |
| PIE7 | KGACDYPEWQWLCAA (SEQ ID NO: 6) |
| PIE8 | KGACDYKEWQWLCAA (SEQ ID NO: 7) |

TABLE 1-continued

D-peptide binding and neutralization

| Sample | Sequence |
|---|---|
| PEG-PIE7 | PEG-KGACDYPEWQWLCAA (SEQ ID NO: 8) |
| PEG-$(PIE7)_2$ | PEG-(KGACDYPEWQWLCAA)2 (SEQ ID NO: 9) |
| 2K-PhD1 | KKGACPREWHWLCAA (SEQ ID NO: 10) |
| PhD1 | GACPREWHWLCAA (SEQ ID NO: 11) |
| 2K-PIE0 | KKGACDYWEWRWLCAA (SEQ ID NO: 12) |
| D-PIE2 | DGACDYPEWRWLCAA (SEQ ID NO: 13) |
| 2K-PIE3 | KKGACDDPDWQWLCAA (SEQ ID NO: 14) |
| 2K-PIE4 | KKGACEDPDWQWLCAA (SEQ ID NO: 15) |
| 2K-PIE5 | KKGACEDPEWQWLCAA (SEQ ID NO: 16) |
| 2K-PIE6 | KKGACNDPEWQWLCAA (SEQ ID NO: 17) |
| PIE1 | DGACESPEWQWLCAAGAA (SEQ ID NO: 18) |
| R4#9 | ACPPEWHWLCGGGSA (SEQ ID NO: 19) |
| R4#12 | ACPVEWRWLCGGGSA (SEQ ID NO: 20) |
| R4#6 | ACPIEWRWLCGGGSA (SEQ ID NO: 21) |
| PhD1b | ACPREWHWLCGGGSA (SEQ ID NO: 22) |
| PIE7-GK | GACDYPEWQWLCAAGK (SEQ ID NO: 23) |
| PIE7-GKK | GACDYPEWQWLCAAGKK (SEQ ID NO: 24) |
| K-PIE7-GK | KGACDYPEWQWLCAAGK (SEQ ID NO: 25) |
| PIE12 | HPCDYPEWQWLCELGK (SEQ ID NO: 26) |
| PIE13 | HPCDYPEWQWLCKLGK (SEQ ID NO: 27) |
| PIE14 | HPCDYPEWQWLCRLGK (SEQ ID NO: 28) |
| PIE15 | HACDYPEWQWLCELGK (SEQ ID NO: 29) |
| Consensus sequence | CDYXEWXWLC (SEQ ID NO: 33) |
| Consensus sequence | $CX_5EWXWLC$ (SEQ ID NO: 34) |
| Consensus sequence | $CX_3EWXWLC$ (SEQ ID NO: 35) |

TABLE 1-continued D-peptide binding and neutralization

| Sample | Sequence |
| --- | --- |
| Consensus sequence | CX$_4$WXWLC (SEQ ID NO: 36) |

The term "D-amino acid residue", as used herein, refers to an α-amino acid residue having the same absolute configuration as D-glyceraldehyde.

Embodiments of the compositions disclosed herein comprise peptides, portions of the peptides, and variations/derivatives of the peptides that can be used as inhibitors of HIV entry into cells. Particular embodiments of the peptides disclosed herein, or a portion of such peptides, that is sufficient to fit into the hydrophobic pocket at the C-terminal end of the coiled-coil and prevent interaction of the C-peptide region with the N-peptide region of gp41, may be useful to inhibit HIV infection. A portion of any of the peptides represented or of a derivative thereof can be from 2 to 20 (any number of residues from 2 to 20) amino acid residues in size. In specific embodiments, D-peptides which comprise at least the consensus sequence EWXWL (SEQ ID NO: 30) or at least the sequence WXWL (SEQ ID NO: 31), can be used. Where D-peptides as described herein include amino acid residues in addition to a consensus sequence, the additional amino acid residues and the size of the D-peptides can be selected with reference to the peptides described herein or can be designed independent of those peptides, provided that peptide can fit into the hydrophobic pocket and act as an inhibitor. Additional amino acid residues can also be present at the N-terminus, the C-terminus or both of the D-peptides described herein, thus producing a larger peptide. Alternatively, there can be other amino acid residues selected, for example, to enhance binding affinity. For example, such a peptide can include the conserved amino acid residues, which can be at the same positions as those at which they occur in the peptides disclosed herein. In some embodiments, the peptide can comprise the core sequence "WXWL" (SEQ ID NO: 31).

In some embodiments of the peptides disclosed herein, the peptides may comprise amino acid residues which can be different from the amino acid residues at these positions in any of the peptides disclosed herein (e.g., can be isoleucine or asparagine or other amino acid residue which does not appear in the peptides disclosed herein) or can be substituted for or replaced by an amino acid residue represented at a specific position in another peptide. Amino acid residues other than the D-versions of the 20 L-amino acids found in natural proteins can be used. Such changes can be made, for example, to enhance bioavailability, binding affinity or other characteristic of the peptide. A D-peptide can comprise the conserved amino acid residues present in the peptides disclosed herein, but they can be separated by fewer (or more) amino acid residues than the number of intervening amino acid residues shown in Table 1. For example, fewer than five amino acid residues can be present between the first cysteine and the glutamic acid in the consensus sequence. Alternatively, these two residues can be separated by more than five amino acid residues. Internal modifications can also be made (e.g., to enhance binding or increase solubility of a peptide). For example, the first leucine of D10p5 can be replaced by an arginine to increase solubility. A D-peptide can have additional moieties or amino acids at its N-terminus. For example, a moiety which blocks the N terminus or gets rid of the charge otherwise present at the N-terminus can be added. The moiety can be, for example, a blocking moiety, such as an acetyl group linked directly to the glycine (G), or an acetyl group linked to one or more additional amino acid residues linked to the N-terminal of G, such as an acetyl group linked to one or more lysine residues, which, in turn, are linked to the N-terminal G.

In one embodiment of the peptides disclosed herein, two lysine residues are linked to the N-terminal G (KKGAC . . . , SEQ ID NO: 32), for example to increase the solubility of the peptide, and then a blocking moiety, such as an acetyl group, can be linked to the terminal lysine (acetyl group-KKGAC . . . , SEQ ID NO: 32). In another embodiment, four lysine residues are linked to the N-terminal G. In addition, a D-peptide can have additional and/or altered moieties or amino acids at its C-terminus. For example, one or both of the alanine residues at the C-terminus can be altered and/or one or more residues can be added at the C-terminus, for example to enhance binding. Alternatively, functional (chemical) groups other than amino acid residues can be included to produce an inhibitor of the embodiments disclosed herein. For example, these additional chemical groups can be present at the N-terminus, the C-terminus, both termini or internally.

Two or more D-peptides can be linked via an appropriate linker (e.g., a linker of amino acid residues or other chemical moieties) to increase the effectiveness of inhibition. Alternatively, one or more D-peptides can be linked via an appropriate linker to a molecule (drug) that binds to HIV gp120, CD4, CCR5, CXCR4, or a non-pocket region of HIV gp41 to increase the effectiveness of inhibition.

Regarding the nomenclature of the peptides disclosed herein, different families of peptides are referred to as x-mers, where x is considered the number of residues between the cysteine residues. The x-mers are referred to as the "core peptides." For example, SEQ ID NO: 6 (KGACDYPEWQWLCAA) is comprised of 15 residues, and so in the standard art would be referred to as a 15-mer. However, in certain embodiments disclosed herein, the length of residues between the cysteines (C) is 8, so it would be considered an 8-mer (and referred to as having 8 core residues), and referred to as such throughout the application. In particular embodiments, amino acids outside of the two Cys residues are referred to as "flanking" sequences. This naming scheme allows different families of peptides that differ in the number of residues between the two Cys residues, but can vary in total peptide length due to differences in their flanking sequences, to be distinguished. For example, SEQ ID NO: 6 (KGACDYPEWQWLCAA) has a length of 15 residues, is a member of the 8-mer peptide family (as it has 8 core residues), and has an N-terminal flanking sequence of KGA and a C-terminal flanking sequence of AA. In comparison, SEQ ID NO: 2 (KKGAC-ESPEWRWLCAA) has a total peptide length of 16 residues, but is also a member of the 8-mer peptide family and contains an N-terminal flanking sequence of KKGA and a C-terminal flanking sequence of AA. In addition to the core residues and flanking residues present on the peptides disclosed herein, all of the peptides disclosed herein may comprise blocked N- and C-termini with the N-termini being blocked by an acetyl group (Ac) and the C-termini being blocked by an amino group (NH$_2$).

As described herein, the D-peptides of the present disclosure can be flanked by GA at the N-terminus and AA at the C-terminus, due to the design of the library used in identifying the D-peptides. Some or all of these amino acid residues may be altered, replaced or deleted in order to produce D-peptides with, for example, altered absorption, distribution, metabolism and/or excretion. In one embodiment, the C-terminus is modified by the addition of a glycine residue immediately before the C-terminal amide. In another embodiment, the most C-terminal A is altered/modified or replaced by a different amino acid residue or deleted. In yet a further embodiment, amino acids are added to the C-terminus and/or N-terminus. Thus, it is contemplated herein that the both the N-terminal GA and C-terminal AA can substituted or additionally flanked to enhance potency. For example one or two lysines can be added to the C-terminal AA to create single or double lysine variants of a particular PIE. Also for example, the N-terminal Lys can be modified to comprise HP at the N-terminus.

One sequence of a D-peptide contemplated by the present disclosure is Ac-HPCDYPEWQWLCELGK-NH2 (SEQ ID NO: 26) which is also referred to as PIE12. In another embodiment, the D-peptide may be PIE7-GK with a sequence of Ac-GACDYPEWQWLCAAGK-NH2 (SEQ ID NO: 23). This peptide is the same as PIE7, except that the Lys has been moved to the C-terminus. The move results in slightly enhanced potency and allows for the crosslinking of peptides via their C-termini. Another example of a PIE7 variant includes PIE7-GKK (GACDYPEWQWL-CAAGKK, SEQ ID NO: 24). This is a double Lys variant of PIE7-GK, and may serve as a central peptide in certain embodiments of a trimeric PIE7 (the central PIE7-GKK is connected to two flanking PIE7-GK peptides). These connections are all via the C-terminus. Also disclosed is K-PIE7-GK (KGACDYPEWQWLCAAGK, SEQ ID NO: 25). This double Lys variant of PIE7-GK can serve as a central peptide in particular embodiments of other embodiments of trimeric PIE7 (the central K-PIE7-GK is connected to two flanking peptides—PIE7-GK and PIE7). These connections link the N- to C-termini of neighboring peptides. Additional examples of variant peptides disclosed herein are the following variants of PIE12: PIE13, HPCDYPEWQWL-CKLGK (SEQ ID NO: 27); PIE14, HPCDYPEWQWLCR-LGK (SEQ ID NO: 28); and PIE15, HACDYPEWQWL-CELGK (SEQ ID NO: 29).

In certain embodiments, the peptides disclosed herein can also be present as multimers, such as dimers or trimers. For example, when the multimer is a dimer, the dimer can be comprised of two identical peptides, or can be comprised of two different peptides. Alternatively, the multimer can also be a trimer. When the multimer is a trimer, the trimer can be comprised of two identical peptides and one different peptide, or three identical peptides, or three different peptides, each of which is distinct from each other.

1. Multimers

Disclosed herein are multimers of the peptides which are described herein. In certain embodiments, the multimers disclosed herein can comprise at least one D-peptide which interacts with the N-trimer pocket of a viral transmembrane protein. The multimer can be a dimer, trimer, or higher order multiples such as a tetramer, but could also include multimers with 5, 6, 7, 8, 9, 10, 11, or 12 D-peptides. Thus disclosed herein are compositions comprising multimers including one or more D-peptide pocket-specific inhibitors of entry (PIE).

It is understood and herein contemplated that the disclosed D-peptides can be crosslinked to form multimers. In certain embodiments, the multimers may be crosslinked through the use of multimer scaffolds. An example of a crosslinker is polyethylene glycol (PEG) derivatized with NHS-ester (reacts with Lys) or maleimide (reacts with Cys). In other embodiments, crosslinkers can also contain two distinct linkage chemistries (e.g., NHS-ester on one end and maleimide on the other end). In particular embodiments, D-peptides may also be linked by direct disulfide bond formation between two Cys residues.

In certain embodiments, the multimer scaffold can be a trimeric scaffold comprising three NHS ester groups. In particular embodiments, the multimer scaffold may be a homotrimeric scaffold or a heterotrimeric scaffold comprising three NHS ester groups. Furthermore, in other embodiments, the multimer scaffold may be a tetrameric scaffold comprising three NHS ester groups and a fourth orthogonal group. In such embodiments, the multimer scaffold may be a heterotetrameric scaffold comprising three NHS ester groups and a fourth orthogonal group. Additionally, particular embodiments of the disclosed crosslinker and multimer scaffold can comprise a tris, di-lysine, benzene ring, phosphate, or peptide core. Other crosslinkers disclosed herein for use with the disclosed compositions comprise thiol-reactive groups, e.g., haloacetyls (e.g., iodoacetate), pyridyl disulfides (e.g., HPDP), and other thiols.

The D-peptides that are linked can be any of those disclosed herein, and the D-peptides can be identical to each other or can each be different. When a dimer is present, the N-termini of both of the D-peptides can be crosslinked to each other. Alternatively, the C-termini of the D-peptides can be crosslinked. Also, the N-terminus of one D-peptide and the C-terminus of the other D-peptide are crosslinked. When a trimer is present, the N-termini and C-termini of the D-peptides can be linked in any combination. For example, they can be linked in any of the following arrangements: N—N/C—C-peptide 1's N-terminus links to peptide 2's N-terminus; peptide 2's C-terminus links to peptide 3's C-terminus. Using this naming, there are 16 possible trimer lineages: X/Y where X and Y=N—N, N—C, C—N, or C—C. D-peptides can also be linked to a central scaffold by the N- or C-termini or an internal location or a combination of these. Thus, for example, it is contemplated herein that one or more D-peptides can be crosslinked at internal residues rather than a terminal crosslinking. It is further contemplated that in trimers an internal crosslinker can be used for one peptide pair (e.g., peptide 1 to peptide 2) and a terminal crosslinker (N- or C-termini) can be used for crosslinking peptide 2 to peptide 3.

As used herein, the naming scheme for multimers describes the way the peptides are connected. For example, C5C-PIE7-trimer means that three PIE7 peptides are connected via C- to C-terminal connections using a PEG$_5$ spacer. N9C-PIE7-trimer means that three PIE7 peptides are connected via N- to C-terminal connections using a PEG$_9$ spacer. Some examples of dimers are as follows: N9C-PIE7-dimer, C9C-PIE7-dimer, N5N-PIE7-dimer, N5C-PIE7-dimer, C5C-PIE7-dimer, N0N-PIE7-dimer, N0C-PIE7-dimer, and C0C-PIE7-dimer. Note: The zero length spacers can be any of a variety of short crosslinkers (e.g., BS3, DSG, or DST). The structure of DSG is as follows:

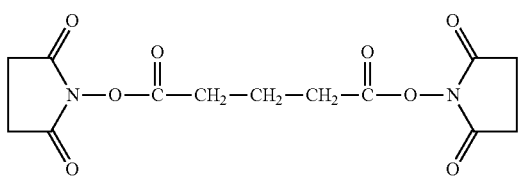

DSG
(Disuccinimidyl Glutarate)
MW 326.26
Spacer Arm Length 7.72 Å

In some embodiments of the compositions disclosed herein, the C5C connection geometry can be used as the linkage for making dimers and trimers. Examples of such dimers include C5C-PIE12-dimer and PEG$_5$-PIE13-dimer (this peptide has an internal Lys residue, and therefore a dimer can be made by crosslinking via this internal Lys). In certain embodiments, a PEG$_5$ linker can be used, for example. Examples of trimers include: C5C-PIE7-trimer, C5C-PIE12-trimer, and the C0C-PIE7-trimer.

As used herein, the term "PIE12-trimer" is a generic term for a multimer that represents a number of molecules with slightly different chemical compositions in which three PIE12 monomers are linked together by various crosslinking strategies. In certain embodiments, one class of PIE12-trimer may be constructed by connecting monomers using PEG crosslinkers of various lengths without use of a central scaffold. In such embodiments, the trimers may be designated, for example, CxC-PIE12-trimer where "CxC" represents linkage of PIE12 monomers via a unique primary amine of a lysine side chain where the lysine residue is located at the C-terminus of the peptide monomer. In other embodiments, NxN-PIE12-trimers represent linkage by a lysine located at the N-terminus. The "x" in this context refers to the number of PEG units in the crosslinker connecting individual monomers. In particular embodiments, a central monomer containing two lysines may be used to make trimers of this type. An alternate name for trimers of this type is, for example, C5C(PIE12)$_3$ where the "3" subscript indicates a trimer.

As described herein, some embodiments of PIE12-trimers may be constructed using a central multimer scaffold containing a trivalent atom (i.e., nitrogen) at its core with three PEG linkers or "arms" of various length connecting PIE12 monomers into a trimer. In other embodiments, the central multimer scaffold may comprise the use of a tetravalent atom at the core of the multimer scaffold (i.e., carbon), with, for example, three PEG linkers of various lengths connecting individual monomers.

In certain embodiments, potency-enhancing versions of PIE12-trimer may be assembled using a carbon core scaffold in which a potency-enhancing cargo moiety is attached to a PIE12-trimer utilizing the fourth arm of the tetravalent scaffold. In such embodiments, PEG units of various length (i.e, 2-132 PEG units) can be used to link various moieties to the 4th arm. One example of a PIE12-trimer is chol-PEG$_{24}$-PIE12-trimer, where "chol" is short for thiocholesterol and "PEG$_{24}$" refers to the number of PEG units comprising the 4th arm. In particular embodiments, the potency-enhancing cargo can be attached to the 4th arm PEG unit by various chemical reactivities including maleimide chemistry. This nomenclature for trimerization applies to other D-peptides described herein (e.g., PIE7 or PIE7-GK).

The multimers disclosed herein can be made of any combination of peptides, including those disclosed in Table 1, or variants thereof, such that the multimers can inhibit viral entry into a cell. In certain embodiments, the multimers can be made up of one of the peptides disclosed herein, two of the peptides disclosed herein, or three or more of the peptides disclosed herein. In such embodiments, all of the peptides can be identical, or they can be any combination of peptides, including those disclosed and those which are not specifically disclosed. In particular embodiments, at least one of the peptides can comprise the sequence WXWL (SEQ ID NO: 31). In other embodiments, the multimers disclosed herein can be made up of at least one D-peptide, two of more different D-peptides, or other components as well.

a) Multimer Scaffold

As an alternate strategy for making multimers, a central multimeric scaffold can be used to attach one or more D-peptides. In particular embodiments, a multimeric scaffold as disclosed herein may comprise a central trifunctional crosslinker tris(succinimidyl) aminotriacetate, such as TSAT, which contains three N-hydroxysuccinimide (NHS) ester groups. In some embodiments, this geometry is referred to as "the claw", as the configuration resembles an eagle claw. Two examples of this strategy are (1) a short claw (which directly links TSAT to the peptides) and (2) a long claw (which uses an extended form of TSAT (LC-TSAT) that contains an additional six-atom spacer between TSAT and the peptides). Other spacer lengths or compositions (e.g., PEG) can also be used. Examples different claw configurations include PIE7-GK (long claw) and PIE7-GK (short claw).

Below is a representation of LC-TSAT:

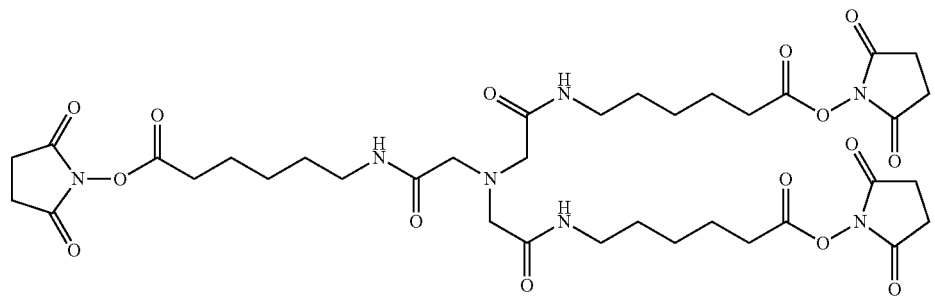 [SMILES: O=C(CN(CC(=O)NCCCCCC(=O)ON1C(=O)CCC1=O)CC(=O)NCCCCCC(=O)ON1C(=O)CCC1=O)NCCCCCC(=O)ON1C(=O)CCC1=O]

And the following is a representation of TSAT:

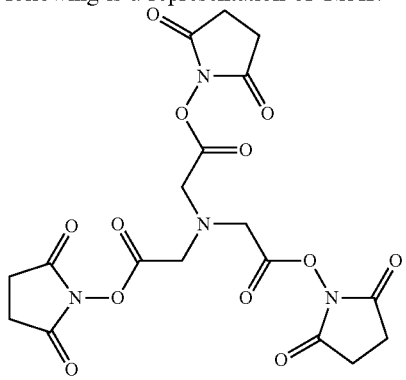

"Over-engineering" future D-peptides means improving affinity even after reaching the potency limit. Such inhibitors do not show improved anti-viral potency in vitro, but have a reserve of binding energy (affinity) that acts as a "resistance capacitor" to defend against potential resistance mutations (i.e., resistance mutations that moderately affect binding affinity would have no effect on potency). This "resistance capacitor" property discourages the stepwise accumulation of multiple subtle mutations that combine to confer resistance. Individual mutations have no effect on inhibitor potency and do not confer a growth advantage in the presence of inhibitors. This "resistance capacitor" may be especially beneficial for trimeric D-peptide inhibitors, because resistance mutations simultaneously affect all three pockets. In certain embodiments, as a further defense against the development of resistance, the trimeric D-peptides disclosed herein can also be constructed by using three different D-peptide sequences, each with a distinct resistance profile. Such a heterotrimer would present a significant additional barrier to the development of resistance.

b) Heterotetramer

As disclosed herein, the PIE12-trimer is a potent inhibitor of HIV entry. In certain embodiments of the compositions disclosed herein, further modifications are contemplated that allow for PIE12 to, 1) be synthesized more easily and in higher yield; 2) to possess enhanced pharmacokinetic properties (e.g., by reducing renal filtration since it is smaller than the glomerular filtration cutoff molecular weight); and 3) to allow for local concentration on the cell surfaces where As used herein, a potency-enhancing cargo is a cargo enhances the potency of the compositions disclosed herein. In some embodiments, a potency-enhancing cargo comprises a cargo that has pharmacokinetic-enhancing properties. In other embodiments, a potency-enhancing cargo comprises a cargo that has membrane-localizing properties. In particular embodiments, the potency-enhancing cargo may comprise a pharmacokinetic-enhancing cargo including any group that will reduce clearance of the peptide. For example, disclosed herein are compositions comprising a multimer scaffold with a potency-enhancing cargo, wherein the potency-enhancing cargo is a sterol (e.g., cholesterol), albumin, polyethylene glycol, a sugar, maltose binding protein, serum albumin, ubiquitin, streptavidin, immunoglobulin domains, keyhole limpet hemacyanin, sperm whale myoovalbumin, bovine pancreatic trypsin inhibitor, green fluorescent protein, gold particles, magnetic particles, agarose beads, lactose beads, or fatty acids. In other embodiments, the potency-enhancing cargo can be the linking of multiple multimers such as the linking of multiple trimers (to increase molecular weight and reduce renal filtration). Thus, for example, disclosed herein are compositions comprising one or more D-peptide pocket-specific inhibitors of entry (PIE), a multimer scaffold, and a potency-enhancing cargo, wherein the potency-enhancing cargo is cholesterol or an analog thereof.

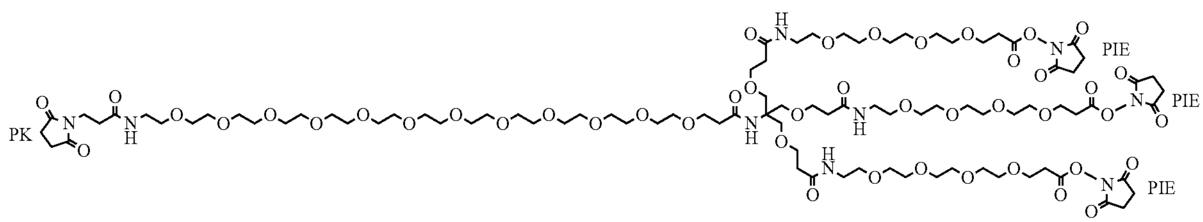

HIV entry takes place, improving potency by overcoming the kinetic potency limit. In particular embodiments, to produce PIE12-trimer variants with some or all of these improved properties, a custom-designed heterotetrameric PEG scaffold can be employed. This scaffold typically has three arms with one type of reactive group (e.g., NHS ester) for attachment of the PIE D-peptide. A fourth group, typically with a longer PEG arm, has a reactive group orthogonal to the other three arms (e.g., maleimide if the three arms have NHS esters). This modular heterotetramer scaffold design allows straightforward modification of any of the PEG arm lengths and significantly simplifies synthesis of trimeric PIEs with appended potency-enhancing cargoes. Below is an example of a heterotetrameric PEG scaffold according to the present description.

In particular embodiments, the compositions disclosed herein include a PIE12-timer with a pharmacokinetic-enhancing cargo exemplified as shown:

Also disclosed herein are PEG linkers. In certain embodiments, the PEGylation that generates a multimer can result in a PEG linker of varying lengths. In particular embodiments, the use of such PEG linkers provides space between the potency-enhancing cargo and the D-peptide pocket-specific inhibitors of entry. It is understood and herein contemplated that the length of the PEG linker can improve $IC_{50}$ and the half-life of the composition. However, too bulky a linker can also have detrimental effects. Thus, disclosed herein are compositions wherein the PEG linker is a linker between the potency-enhancing cargo and D-peptide pocket-specific inhibitors of entry comprising between 12

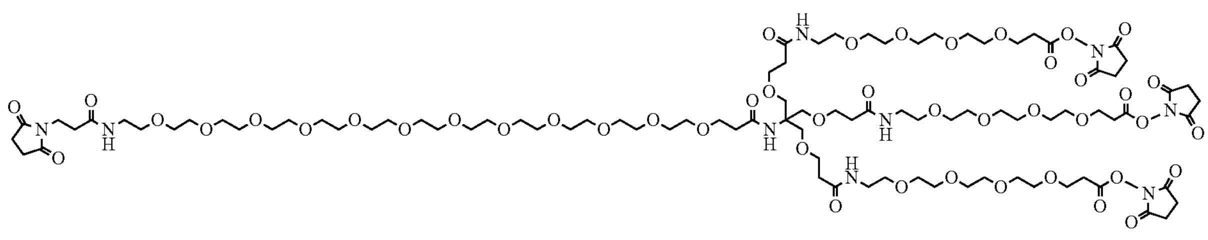 [SMILES: O=C(CCOCC(COCCC(=O)NCCOCCOCCOCCOCCC(=O)ON1C(=O)CCC1=O)(COCCC(=O)NCCOCCOCCOCCOCCC(=O)ON1C(=O)CCC1=O)NC(=O)CCOCCOCCOCCOCCOCCOCCOCCOCCOCCOCCOCCOCCNC(=O)CCN1C(=O)CCC1=O)NCCOCCOCCOCCOCCC(=O)ON1C(=O)CCC1=O]

In certain embodiments, the disclosed compositions comprise a multimer scaffold, such as a heterotetramer scaffold, that can be modified to comprise a potency-enhancing cargo.

and 48 ethylene glycol repeats. Accordingly disclosed herein are PEG linkers with 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 ethylene glycol repeats, referred to as $PEG_{12}$, $PEG_{13}$, $PEG_{14}$, $PEG_{15}$, $PEG_{16}$, $PEG_{17}$, $PEG_{18}$, $PEG_{19}$, $PEG_{20}$, $PEG_{21}$, $PEG_{22}$, $PEG_{23}$, $PEG_{24}$, $PEG_{25}$, $PEG_{26}$, $PEG_{27}$, $PEG_{28}$, $PEG_{29}$, $PEG_{30}$, $PEG_{31}$, $PEG_{32}$, $PEG_{33}$, $PEG_{34}$, $PEG_{35}$, $PEG_{36}$, $PEG_{37}$, $PEG_{38}$, $PEG_{39}$, $PEG_{40}$, $PEG_{41}$, $PEG_{42}$, $PEG_{43}$, $PEG_{44}$, $PEG_{45}$, $PEG_{46}$, $PEG_{47}$, $PEG_{48}$, respectively.

It is also understood that PEG linkers can be used to link the PIE arms to the scaffold. In certain embodiments, in linking the D-peptide pocket-specific inhibitors of entry to the scaffold, the PEG linkers can comprise 2, 3, 4, 5, 6, 7, or 8 ethylene glycol repeats.

Thus, it is understood that the disclosed compositions can comprise the culmination of all the features disclosed herein such as one or more D-peptides, multimer scaffolding, potency-enhancing cargo, and modification of the flanking regions of D-peptides, and PEG linkers. Accordingly, disclosed herein are compositions comprising one or more D-peptides and a potency-enhancing cargo, wherein the one or more D-peptides are linked by a multimer scaffold, wherein the multimer scaffold is linked to the D-peptides via a PEG linker, and wherein the potency-enhancing cargo is linked to the multimer scaffold via a PEG linker.

The multimer scaffold as disclosed herein may be use for a multimer scaffold-based design method for multimeric D-peptide drug optimization (both peptide geometry and localization to the site of action via conjugated localizing cargoes). In certain embodiments, multimer scaffold-based design allows for alterations in the scaffold to accommodate a variety of cargoes and chemistries (e.g., "click" chemistry), as well as rapid optimization of PEG arm lengths. For example, for viruses that undergo membrane fusion within the endosome, such as HIV and Ebola, the multimer scaffold-based strategies disclosed herein could be employed to identify and attach an endosome-targeting moiety to localize an inhibitor to the site of virus entry and increase inhibitor potency. Additionally, particular embodiments of the multimer scaffold-based strategy as disclosed herein may allow for the identification of, and conjugation to a variety of potency-enhancing cargoes to modulate pharmacokinetic properties (e.g., large branched PEGs, albumin, or albumin-binding peptides) and membrane localization.

c) Avidity of Multimers

Disclosed herein are compositions comprising a multimer as disclosed herein and an N-trimer molecule, wherein the multimer, when associated with the N-trimer molecule, has an increased affinity for the N-trimer molecule, when compared with the affinity of a single peptide, or control peptide, for the N-trimer molecule. The single peptide, or control peptide, can be identical to one of the components of the multimer, or the single peptide can be a different peptide which is not contained in the multimer.

The multimer can exhibit about a 2-fold, 3-fold, 4-fold, 5-fold, 10-fold, 20-fold, 25-fold, 30-fold, 40-fold, 50-fold, 100-fold, 200-fold, 300-fold, 400-fold, 500-fold, 1000-fold, 2000-fold, 3000-fold, 4000-fold, 5000-fold, or 10,000-fold increase in affinity for the N-trimer when compared with the affinity of one of the components of the multimer alone.

The multimer can have any of the characteristics or properties that are disclosed herein. Any of the multimers disclosed herein are capable of having avidity as described herein, and any of them can be used with the methods disclosed herein for increasing inhibition of viral entry.

d) Peptide Variants

Also disclosed herein are variants of the peptides described herein and that are herein contemplated. Peptide variants and derivatives thereof are well understood to those of skill in the art and in can involve amino acid sequence modifications. Those peptides disclosed herein that can be used to inhibit viral entry can comprise such amino acid sequence modifications. One of skill in the art would be able to readily determine which modifications can be made in order to retain the activity of the peptide.

Analogs of the peptides disclosed herein are also contemplated. These analogs include one or more D-amino acids of the peptide structure which are substituted with a homologous amino acid such that the properties of the original peptide are maintained. In certain embodiments, conservative amino acid substitutions may be made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Non-limiting examples of homologous substitutions that can be made in the peptide structures of the peptides disclosed herein include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain. This is given as an example and is not intended to be limiting. One of skill in the art would be capable of making conservative substitutions to a D-peptide.

It is further understood that each D-peptide disclosed herein comprises particular residues that contact the pocket of the deep groove in the N-trimer region of gp41. For example, residues 2, 3, 4, 8, 9, 11, 12, and 15 are contact residues of PIE7 and residues 2, 3, 7, 8, 10, 11, and 14 are contact residues of PIE12. In both PIE7 and PIE12 the residues corresponding to E, W, W and L form the core sequence EWXWL (SEQ ID NO: 30) and comprise the internal most contact residues (residues 8, 9, 11, and 12 for PIE7 and residues 7, 8, 10, and 11 for PIE12). It is contemplated herein that making substitutions at the contact residues can significantly affect the binding affinity of the D-peptide for the deep groove. Residues more amenable to change are non-contact residues and contact residues at the C-terminal and N-terminal ends of the peptide.

It is understood that the description of conservative mutations and homology can be combined together in any combination, such as embodiments that have at least 70% homology to a particular sequence wherein the variants are conservative mutations.

The opposite stereo-isomers of naturally occurring peptides are disclosed, as well as the stereo-isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include CH2NH—, —CH2S—, —CH2-CH2-, —CH═CH— (cis and trans), —COCH2-, —CH(OH) CH2-, and —CHH2SO— (these and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—CH2NH—, CH2CH2-); Spatola et al. Life Sci 38:1243-1249 (1986) (—CH H2-S); Hann J. Chem. Soc Perkin Trans. I 307-314 (1982) (—CH—CH—, cis and trans); Almquist et al. J. Med. Chem. 23:1392-1398 (1980) (—COCH2-); Jennings-White et al. Tetrahedron Lett 23:2533 (1982) (—COCH2-); Szelke et al. European Appln, EP 45665 CA (1982): 97:39405 (1982) (—CH(OH)CH2-); Holladay et al. Tetrahedron. Lett 24:4401-4404 (1983) (—C (OH)CH2-); and Hruby Life Sci 31:189-199 (1982) (—CH2-S—); each of which is incorporated herein by reference. An alternative non-peptide linkage is —CH2NH—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

2. Pharmaceutical Carriers/Delivery of Pharmaceutical Products

The peptides and multimers disclosed herein (alternatively referred to as compositions) can also be administered in vivo in a pharmaceutically acceptable carrier. By "pharmaceutically acceptable" is meant a material that is not biologically or otherwise undesirable, i.e., the material may be administered to a subject, along with the peptide disclosed herein, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, by subcutaneous injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disease, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system (i.e., depot) such that a constant dosage is maintained. See, e.g., U.S. Pat. No. 3,610,795, which is incorporated by reference herein.

a) Pharmaceutically Acceptable Carriers

The compositions, including peptides and multimers thereof, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution may be from about 5 to about 8, and alternatively from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed peptides and multimers thereof can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable. Additionally, it is contemplated herein that compositions designed for oral administration can further comprise gut permeabilizing agents.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions disclosed herein, including the peptides and multimers thereof disclosed herein, may be determined empirically, and making such determinations is within the skill in the art. The dosage ranges for the administration of the compositions are those large enough to produce the desired effect in which the symptoms/disorder is affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products, particularly for D-peptides. Examples of such guidance can be found throughout the literature. For example, the peptide FUZEON®, which has been FDA approved, can act as a guide for the dosages required for the peptides disclosed herein. In one embodiment, the typical daily dosage of the peptides or multimers thereof used alone might range from about 1 µg/kg to up to 100 mg/kg of body weight or more per day, depending on the factors mentioned above. Furthermore, the peptides disclosed herein can be administered several times daily, daily, weekly, monthly, or yearly, depending on the condition of the subject, other modes of therapy, etc. One of skill in the art could readily ascertain an appropriate dosing schedule.

Following administration of a disclosed composition, such as a peptide for treating, inhibiting, or preventing a viral infection, such as HIV, the efficacy of the peptide or multimer thereof can be assessed in various ways well known to the skilled practitioner. For instance, one of ordinary skill in the art will understand that a composition, such as a D-peptide, disclosed herein is efficacious in treating or inhibiting a viral infection in a subject by observing that the composition inhibits viral entry. Efficacy of the administration of the disclosed composition may also be determined by measuring the number of uninfected cells in the infected subject. A treatment that inhibits an initial or further decrease in uninfected cells in a subject or patient, or that result in an increase in the number of uninfected cells in, for example, the HIV-positive subject, is an efficacious treatment. The efficacy of a prophylactic treatment (i.e., preventative agent) can also be evaluated using indirect measures of infection, such as CD4+ cell counts, levels of anti-virus antibodies, and PCR to detect viral RNA levels.

The compositions that inhibit viral entry, i.e., microbicides, disclosed herein may be administered prophylactically to patients or subjects who are at risk for being exposed to a virus such as HIV or who have been newly exposed to HIV. In subjects who have been newly exposed to a virus such as HIV but who have not yet displayed the presence of the virus (as measured by PCR or other assays for detecting the virus) in blood or other body fluid, treatment with a peptide or multimer thereof includes administering a therapeutically effective dose of a composition, a peptide or multimer as described herein to the subject such that the ability of the virus to infect cells is partially or completely inhibited.

The disclosed peptides can be used to inhibit viral entry by inhibiting viral transmembrane protein. The term "inhibit viral transmembrane protein" refers to a reduction in the number of viral particles that are capable of entering a cell. It can mean complete inhibition, in other words no viral particles are capable of entering a cell, or it can mean a partial inhibition, meaning that in a given system there is a reduction in the number of viral particles capable of entering a cell when compared with a non-treated system, or a control. There can be a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% reduction in the number of viral particles that are capable of entering a cell, or any amount greater, less, or in between these amounts. Additionally, to "inhibit viral entry" means to reduce fusion and entry of virions into a cell.

3. Chips and Micro Arrays

Disclosed are chips where at least one address is the sequences or part of the sequences set forth in any of the peptide sequences disclosed herein.

Also disclosed are chips where at least one address is a variant of the sequences or part of the sequences set forth in any of the peptide sequences disclosed herein.

4. Computer Readable Mediums

It is understood that the disclosed peptides can be represented as a sequence consisting of the amino acids. There are a variety of ways to display these sequences, for example the amino acid valine can be represented by Val or V. Those of skill in the art understand how to display and express any peptide sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the peptide sequences are recorded, stored, or saved.

5. Compositions Identified by Screening with Disclosed Compositions a) Combinatorial Chemistry The disclosed peptides can be used as targets for any combinatorial technique to identify molecules or macromolecular molecules that interact with the disclosed compositions in a desired way. The peptides and related molecules disclosed herein can be used as targets for the combinatorial approaches. Also disclosed are the compositions that are identified through combinatorial techniques or screening techniques in which the compositions disclosed in SEQ ID NOS: 1-36 for example, or portions thereof, are used as the template in a combinatorial or screening protocol.

It is understood that when using the disclosed compositions in combinatorial techniques or screening methods, molecules, such as macromolecular molecules, will be identified that have particular desired properties such as inhibition or stimulation of gp41 interactions. The molecules identified and isolated when using the disclosed compositions, such as other peptides, are also disclosed. Thus, the products produced using the combinatorial or screening approaches that involve the disclosed compositions, such as peptides, are also considered herein disclosed.

b) Computer Assisted Drug Design

The disclosed peptides and multimers thereof can be used as targets for any molecular modeling technique to identify either the structure of the disclosed peptides or multimers or to identify potential or actual molecules, such as small molecules, which interact in a desired way with the disclosed compositions. The peptides and related molecules disclosed herein can be used as targets in any molecular modeling program or approach.

It is understood that when using the disclosed compositions in modeling techniques, molecules, such as macromolecular molecules, will be identified that have particular desired properties such as viral inhibition. The molecules identified and isolated when using the disclosed compositions, such as peptides and multimers thereof, are also disclosed. Thus, the products produced using the molecular modeling approaches that involve the disclosed compositions are also considered herein disclosed.

Generally, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic or NMR analysis of the selected molecule. Molecular dynamics simulations require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario.

Although described above with reference to design and generation of compounds which could alter binding, one could also screen libraries of known compounds, including natural products or synthetic chemicals, and biologically active materials, including proteins.

6. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include a pharmaceutical composition comprising a peptide or multimer thereof as disclosed herein. For example, disclosed is a kit for treating HIV, comprising a pharmaceutical composition comprising a peptide or multimer thereof as disclosed herein.

7. Compositions with Similar Functions

It is understood that the peptides disclosed herein have certain functions, such as inhibiting viral entry. Disclosed herein are certain structural requirements for performing the disclosed functions, and it is understood that there are a variety of structures which can perform the same function which are related to the disclosed structures, and that these structures will ultimately achieve the same result, for example inhibiting viral entry.

C. Methods of Making the Compositions

The compositions disclosed herein and the compositions necessary to perform the disclosed methods can be made using any method known to those of skill in the art for that particular reagent or compound unless otherwise specifically noted.

1. Peptide Synthesis

The peptides disclosed herein can be linked, for example, by disulfide crosslinks. For example, the D-peptides disclosed herein have two Cys residues connected by a disulfide bond, which circularizes the peptide and creates a more compact and structured peptide. This disulfide is known to have enhanced antiviral properties. There are many alternative methods for circularizing peptides known to those of skill in the art. For example, a peptide can be circularized using lactam or other chemical bridges, PEG or other chemical crosslinkers, peptide ligation, or diselenide bonds (between selenocysteines).

Two or more peptides or polypeptides can also be linked together by protein chemistry techniques. For example, peptides or polypeptides can be chemically synthesized using currently available laboratory equipment using either Fmoc (9fluorenylmethyloxycarbonyl) or Boc (tert butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. SpringerVerlag Inc., NY (which is herein incorporated by reference at least for material related to peptide synthesis). Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776779 (1994)). The first step is the chemoselective reaction of an unprotected synthetic peptidethioester with another unprotected peptide segment containing an aminoterminal Cys residue to give a thioester linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; ClarkLewis I et al., J. Biol. Chem., 269:16075 (1994); ClarkLewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (nonpeptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257267 (1992)).

Mirror-image phage display can be used to discover D-peptides that bind to the N-trimer pocket and inhibit HIV-1 entry with modest potency. For example, in using mirror-image phage display to screen for D-peptides, a first D-peptide can be synthesized from the first L-peptide from a HIV glycoprotein. The first L-peptide can be a naturally occurring L-peptide or can be a chimera of designed peptide sequences and natural peptide sequences. The methods can further comprise screening for a second L-peptide that specifically binds to the first D-peptide; then, a second D-peptide that is the mirror image of the second L-peptide can be synthesized. In one aspect of the D-peptide screening methods described herein, an N-trimer target can first be synthesized with D-amino acids, creating the mirror image of the natural L-N-trimer target. The D-N-trimer target can be used in standard peptide-based screens such as phage display, ribosome display, and/or CIS display to identify L-peptides that bind to the D-N-trimer. The identified L-peptides can then be synthesized with D-amino acids. By the law of symmetry, the resulting D-peptides bind the natural L-N-trimer, and will thus target the N-trimer region of the HIV prehairpin intermediate, thereby treating or inhibiting HIV infection. This screening method is also described in Schumacher, et al., Identification of D-peptide ligands through mirror-image phage display, Science, 1996 Mar. 29; 271(5257):1854-7, which is hereby incorporated in its entirety by this reference.

D. Methods of Using the Compositions

1. Methods of Using the Compositions as Research Tools

Disclosed herein are methods for evaluating the ability of a composition comprising a peptide of less than 10 core residues in length for its ability to inhibit viral entry into a cell comprising: incubating the composition and a cell under conditions sufficient to allow the components to interact; contacting the components with a virus; and evaluating the ability of the composition to inhibit viral entry into the cell. The peptide can comprise less than 7, 8, 9, or 10 core amino acid residues. The peptide can be present as a multimer, as disclosed above. The composition can inhibit viral entry by interacting with a viral transmembrane protein, such as HIV gp41. The peptide can be a D-peptide. Furthermore, evaluating the ability of the composition to inhibit viral entry can be by detection of a reporter means. Examples of such reporter means include, but are not limited to, a radioisotope, a fluorescent compound, a bioluminescent compound, a chemiluminescent compound, a metal chelator, or an enzyme. Evaluating the ability of the composition to inhibit viral entry into the cell can be done by evaluating the ability of the composition to be displaced from its binding site (the gp41 N-trimer pocket) by other compounds (e.g., peptides, small molecules, nucleic acids, natural products). By “displaced” is meant that the composition is inhibited from binding, or is disrupted from its interaction with the binding site. This can occur at 5, 10, 15, 20, 25, 30, 35, 40, 45, 50, 55, 60, 65, 70, 75, 80, 85, 90, 95, or 100% displacement of the test compositions from the binding site.

The ability of the composition to inhibit viral entry can be measured using viral entry assays or cell-cell fusion assays. Viral entry assays are known to those in the art, as are cell-cell fusion assays. One can use a displacement assay comprising other compounds that can displace the test composition from the binding site. Examples include, but are not limited to, peptides, small molecules, nucleic acids, or natural products. Such displacement assays are known to those of skill in the art.

Also disclosed is a method of identifying a multimer with increased affinity for an N-trimer molecule when compared with the affinity of one of a single peptide, comprising: incubating the multimer and an N-trimer molecule; measuring the affinity of the multimer for the N-trimer molecule; and comparing the affinity of the multimer for the N-trimer molecule with the affinity for the N-trimer molecule of a single peptide.

Further disclosed is a method of identifying a multimer with enhanced antiviral activity for an N-trimer molecule when compared with the antiviral activity of one a single peptide, comprising: incubating the multimer with a cell; contacting the components of step (a) with a virus; measuring the antiviral activity of the multimer; and comparing the antiviral activity of the multimer with the antiviral activity of a single peptide. The single peptide can be identical to one of the components of the multimer, or can be different. The multimer can comprise at least one peptide which interacts with the N-trimer pocket of viral gp41.

Inhibition of complex formation of gp41 can be assessed by determining the extent to which binding of the two members of the complex occurs, such as by means of a fluorescence assay (e.g., FRET), in which C34 and N36 are each labeled by a member of a pair of donor-acceptor molecules or one end of one of the peptides (e.g., the N-terminus of C34) is labeled with one member of such a pair (EDANS) and the natural fluorophore tryptophan, present in the N36 peptide, is the other member of the donor/acceptor pair. Binding of the C34 and N36 is assessed by the extent to which light emission (FRET) occurs from the acceptor model and/or the wavelength spectrum of the light emitted is altered. Prevention of binding by the candidate drug alters the extent to which light is emitted and/or prevents the shift in wavelength that would occur if binding of C34 and N36 occurred. Alternatively, C34 can be labeled with a detectable label, such as a radiolabel (e.g., by synthesizing a variant C34 with a kinase recognition site that can be labeled with a kinase and radioactive ATP). The radiolabeled C34 and the candidate drug are combined with N36 immobilized to, for example, a solid surface (e.g., a bead or a plastic well), thus producing a test sample. The extent to which binding of labeled C34 with immobilized N36 occurs is determined and compared with the extent to which binding of labeled C34 to immobilized N36 occurs under the same conditions to which the test sample is subjected, but in the absence of the candidate drug (in a control sample). Typically, this assessment is carried out after the sample has been maintained for sufficient time and under appropriate conditions for C34/N36 binding to occur and a subsequent wash to remove any unbound C34 and candidate drug. If binding occurs in the test sample to a lesser extent than in the control sample, as evidenced by less radiolabel bound to the immobilized N36 in the test sample than in the control sample, the candidate drug is an inhibitor of binding of C34 and N36. Alternatively, the label or tag on C34 can be a member of a binding pair, the other member of which is used to detect binding to N36. For example, C34 can be tagged with biotin (through standard solid-state peptide synthesis, for example) and combined with N36, which can be in solution or bound to a solid surface, such as a bead, well or flat/planar surface, along with the candidate drug (test sample) or in the absence or the candidate drug (control sample). Binding of C34 to N36 is assessed by detecting the presence of biotin associated with N36, such as through the use of labeled streptavidin (e.g., streptavidin—HRP, streptavidin—AP or iodinated streptavidin), which binds the biotin on C34 and is then itself detected through its label. If binding occurs less in the presence of the candidate drug (in the test sample) than in the absence of the candidate drug (in the control sample), as indicated by the presence of less biotin detected on N36 in the test sample than in the control sample, the candidate drug is an inhibitor of C34/N36 binding. The candidate drugs can be obtained, for example, from a library of synthetic organic compounds or random peptide sequences, which can be generated synthetically or through recombinant technology.

In a similar fashion, the ability of a candidate drug to disrupt C34/N36 binding can be assessed, to identify inhibitors of C34/N36 and, thus, of HIV infection. In this embodiment, preformed C34/N36 complex is combined with a candidate drug, which is to be assessed for its ability to disrupt the complex, thus producing a test sample. The control sample is the same as the test sample, except that the control sample does not contain the candidate drug; it is treated in the same manner as the test sample. If C34/N36 binding is disrupted in the presence of the candidate drug and not in the control sample or if disruption of the complex occurs to a greater extent in the test sample than in the control sample, the candidate drug is an inhibitor (disrupter) of C34/N36. Detection of disruption of binding can be carried out as described above for detection of/prevention of/interference with binding of C34/N36 (e.g., by FRET or a fluorescence assay, by detecting a radiolabel or other detectable label, such as biotin.)

In another embodiment, the current disclosure relates to a method of identifying a drug that binds the N-helix coiled-coil cavity of HIV gp41. Here, too, the assay is based on assessing loss or decrease in binding, but unlike the C34/N36 complex assay described above, which is a more general assay in that it covers or detects interaction with any portion of the groove formed by the N-helical region of HIV gp41, this embodiment focuses on the HIV gp41 hydrophobic pocket (the N-helix coiled-coil cavity). In this embodiment, the method comprises combining a candidate drug to be assessed for its ability to bind the N-helix coiled-coil cavity of HIV gp41 with a fusion protein that comprises a trimeric version of the coiled-coil region of a protein and a sufficient portion of the N-peptide of HIV gp41 to include the HIV gp41 cavity, under conditions appropriate for presentation of the HIV gp41 cavity for binding by a peptide or other molecule and determining (e.g., in a high throughput screen) whether the candidate drug binds the fusion protein. If binding occurs, the candidate drug is a "hit" that may be a drug that binds the N-helix coiled-coil cavity of HIV gp41. If binding occurs, the candidate drug has bound the N-helix coiled coil and it can be determined if it binds to the coiled-coil cavity. Such "hits" can then be screened in secondary assays, such as the cell/cell fusion assay and HIV infectivity assay to determine if the candidate drug is a drug. Alternatively, or in addition, such "hits" can be assessed further by use of a counterscreen with other fusion proteins (or peptides), to which pocket-binding molecules will not bind.

In a further embodiment, a competitive assay is carried out. In this embodiment, a peptide or protein that binds the N-helix coiled-coil cavity of HIV gp41 is combined with the candidate drug and the fusion protein and whether the candidate drug binds the HIV gp41 cavity is determined in the presence of the peptide that binds the N-helix coiled cavity of HIV gp41. If the candidate drug binds the fusion protein, it is a drug that binds the HIV gp41 cavity. For example, a fusion protein which comprises a trimeric version of the coiled-coil region of GCN4 and the C-terminus of the N peptide of HIV gp41 that includes the N-helix coiled-coil cavity (IQN17) is combined with a "reference" D-peptide (e.g., any of the D-peptides described herein or variants thereof) that binds the N-helix coiled-coil cavity and a candidate drug to be assessed for its ability to bind the N-helix coiled-coil cavity of HIV gp41, thus producing a test sample, which is maintained under conditions appropriate for binding of the D-peptide to bind to the cavity. A control sample, which includes the same components as the test sample, except for the candidate drug, and is handled in the same manner as the test sample, is also assessed. In both samples, binding of the reference D-peptide is assessed. If binding of the reference D-peptide occurs to a lesser extent in the presence of the candidate drug (in the test sample)

than in its absence (in the control sample), the candidate drug is a drug that binds the N-helix coiled-coil cavity of HIV gp41. Detection of binding is assessed, for example, in a similar manner as described above for the C34/N36 embodiment of the disclosure. For example, the D-peptide is labeled with a detectable label, such as a radiolabel or a first member of a binding pair (e.g., biotin), and the extent to which the N-helix coiled-coil cavity bears the label (after the samples have been maintained under conditions appropriate for binding of the reference D-peptide to the cavity) is determined. In the case in which radiolabeling is used, the extent to which the fusion protein bears the radiolabel is assessed in the test sample and compared with the extent to which the fusion protein bears the radiolabel in the control sample. If the detectable label is a first member of a binding pair (e.g. biotin), the second member of the pair (a binding partner) is added to the samples in order to detect the extent to which the fusion protein is bound by the reference D-peptide. This can be done directly or indirectly (e.g., by adding a molecule, such as an antibody or other moiety which binds the second member of the binding pair). Less of the label will be present on the fusion protein (N-helix coiled-coil cavity) if the candidate drug has inhibited (totally or partially) binding of the D-peptide to the cavity. If binding occurs to a lesser extent in the test sample (in the presence of the candidate drug) than in the control sample (in the absence of the candidate drug), then the candidate drug is a drug that binds the N-helix coiled-coil cavity of HIV gp41.

IQN17, or a variant thereof, in the D-enantiomer, is useful to identify molecules or compounds which are members of a library or collection and bind the N-helix coiled-coil of gp41. For example, a library or collection of molecules or compounds, such as a phage display library, can be screened with IQN17 in the D-enantiomer to identify members that bind the pocket. This has been carried out successfully, as described herein. The mirror image of IQN17, or a variant thereof, is used as the target molecule. As used herein, the terms "D-enantiomer of a polypeptide" and "D-peptide" refer to the exact mirror image of the molecule in the natural handedness. Thus, for amino acid residues that contain a second chiral center, such as Ile and Thr, the exact mirror image of the naturally-occurring amino acid residue is used to create the D version of the polypeptide. Also as used herein, the terms "D-amino acids" and "L-amino acids" are both meant to include the non-chiral amino acid glycine. D-IQN17 can be immobilized to a solid surface, such as by addition of one member of a binding pair (e.g., biotin) to it and addition of the other member of the pair (e.g., streptavidin) to the solid surface. Binding of the two members results in immobilization of D-IQN17 on the solid surface, such as for phage panning. A linker which is an enzyme recognition site (e.g., an amino acid linker such as Gly-Lys-Gly, in which an L-lysine residue is used) can be placed between the D-IQN17 sequence and the binding pair member (between the biotin and D-IQN17) to provide an enzyme recognition site (here, a trypsin recognition site), so that bound phage can be eluted by a trypsin digestion, rather than by non-specific elution, such as acid addition. The phage display library can be a library of L-amino acid peptides of any appropriate length fused to an appropriate phage gene. In one embodiment, it is a phage display library of L-amino acid peptides fused to the gIII gene of M13 phage. The peptides, in one embodiment, comprise 10 randomly encoded amino acid residues flanked by either a cysteine or a serine on both sides. Typically, several rounds of panning are carried out. D-IQN17-specific binding phage are identified. Phage that bind only the gp41 region of D-IQN17 can be identified by post-panning assessment, such as by screening against wells that lack the antigen and then further testing against a panel of molecules. For example, specific pocket-binding phage include those that bind DIQN17 but not D-GCN4-pIQI (with the same three surface mutations as in IQN17) or a version of D-IQN17 with a point mutation in the hydrophobic pocket, D-IQN17(G39W), in which glycine 39 is mutated to tryptophan, resulting in a large protrusion into the pocket. D-peptides identified in this manner can be assessed for their ability to inhibit HIV gp41, using known assays, such as the cell/cell fusion assay and HIV infectivity assay. The mirror-image phage display method described herein has demonstrated the value of IQN17 and IQN17 (G39W), and their D-enantiomers in identifying inhibitors of HIV-1 entry that bind the gp41 pocket. Of nine specific pocket-binding phage sequences identified (phage that bind to D-IQN17 but not to D-IQN17(G39W), eight contain a consensus EWXWL sequence and inhibit HIV-1 gp41-induced syncytia formation when tested as D-peptides. The ninth peptide was toxic to cells and was not investigated further.

The D-versions of IQN17 and IQN17(G39W) can be used in a similar manner with other biologically encoded libraries, to discover other pocket-binding molecules that are not subject to enzymatic degradation by natural enzymes. For example, other phage-display libraries can be used to identify new D-peptide inhibitors (e.g., with a different number of residues between the flanking Cys residues and/or with randomly encoded amino acid residues outside the regions flanked by cysteine residues and/or with more than two cysteine residues). Strategies for encoding peptide libraries without phage (e.g., in which the encoding mRNA is attached to the peptide) can be used to identify D-peptide inhibitors. RNA or DNA libraries can be used (e.g., with SELEX methods) to identify L-ribose- or L-deoxyribose-based RNA or DNA aptamers, respectively, that bind to the hydrophobic pocket and are not substrates for natural nucleases (see e.g., Williams et al., PNAS, 74:11285 (1997)).

Although the versions of IQN17 and IQN17(G39W) of natural L-handedness can also be used in similar manner with biologically encoded libraries, the most likely applications will be with other, non-biologically encoded libraries. For example, chemical combinatorial libraries on beads (of the one-bead, one-compound variety) can be screened with labeled IQN17 (e.g., radioactive or with a chromophore) to identify beads containing molecules that bind to IQN17. In this example, IQN17(G39W) can be used as a counterscreen to determine if the molecules on the bead bind to the pocket of IQN17. (If they bind to IQN17(G39W), then they are not likely to be pocket-binding molecules.) As another example, beads to which IQN17 had been previously attached can be incubated with a mixture of potential pocket-binding molecules (e.g., a mixture of chemicals, or a natural product extract). IQN17 (bound to the beads) can then be separated from the mixture, washed, and then subjected to conditions (e.g., organic solvent, low pH, high temperature) that elute molecules bound to the IQN17 on the beads. The eluted molecules (i.e., potential pocket-binding molecules) could be identified by analytical chemistry methods (e.g., HPLC, mass spectrometry). A counterscreen with IQN17(G39W) is useful to help to identify true pocket-binding molecules.

Drugs identified by the methods described above are then further tested for their ability to inhibit (totally or partially) HIV gp41 function (membrane fusion) and, thus entry into cells, using further in vitro assays, such as the syncytium assays and/or infectivity assays described herein or others known to those of skill in the art, and/or in vivo assays in appropriate animal models or in humans.

One embodiment of the present disclosure is a method of identifying a drug that binds the N-helix coiled-coil of HIV gp41, particularly the N-helix coiled-coil pocket. The method comprises combining a candidate drug to be assessed for its ability to bind the N-helix coiled-coil pocket of HIV gp41 and peptide which comprises a soluble, trimeric coiled-coil and a sufficient portion of the N-peptide of HIV gp41 to include the HIV gp41 pocket, under conditions appropriate for presentation of the HIV gp41 pocket for binding by a molecule or compound (e.g., a drug) and determining whether the candidate drug binds the HIV gp41 pocket. If binding of the candidate drug with the HIV gp41 pocket occurs, the candidate drug is a drug which binds the N-helix coiled-coil pocket of HIV gp41. Optionally, binding of the candidate drug can be assessed in the assay as described above, except that a peptide that binds the N-helix coiled-coil pocket (a peptide previously identified as one which binds the pocket) is combined with the candidate drug and the peptide. In this competitive assay, binding of the candidate drug to the N-helix coiled-coil pocket is assessed in the presence of a known binding moiety (a molecule or compound which binds the pocket). If binding of the candidate drug occurs in the presence of the known binding moiety, the candidate drug is a drug which binds the N-helix coiled-coil pocket with sufficient affinity to successfully compete with the known binding moiety. The fusion protein used in this embodiment comprises a soluble, trimeric version of a coiled-coil, such as a soluble, trimeric version of the coiled-coil region of a protein and a sufficient portion of the N-peptide of HIV gp41 to include the HIV gp41 cavity. Alternatively, a variant of the HIV gp41 sequence present herein, a sequence from another strain of the human virus (e.g., HIV-2) or a sequence from another species (e.g., SIV, feline immunodeficiency virus, Visna virus (M. Singh et al., J. Mol. Biol., 290:1031 (1999)) can be used in the fusion protein or soluble model. The fusion protein can comprise a soluble, trimeric version of the coiled-coil of any protein, provided that when it is in the fusion protein with the HIV component, the HIV cavity is presented in such a manner that it is available for binding. It can be, for example, that of GCN4-pIQI, GCN4-pII, Moloney Murine Leukemia Virus (Mo-MLV) or the ABC heterotrimer. In one embodiment, the fusion protein is IQN17 in the D-form. In another embodiment, the fusion protein is IQN17 in the natural L-handedness.

In the competitive assay format, any peptide known to bind the N-helix coiled-coil cavity can be used as the known binding moiety. For example, any of the peptides described herein or a variant or portion thereof can be used. Also, any non-peptide pocket-binding molecule can be used in the competitive assay format. The competitive assay can be performed in solution, on a bead, or on a solid surface.

In one embodiment, the candidate drug is detectably labeled and binding of the candidate drug to the HIV gp41 N-helix coiled-coil is determined by detecting the presence of the detectable label on the HIV gp41 N-helix coiled-coil (as a result of binding of the labeled candidate drug to the N-helix coiled-coil). Detection of the label on the helix coiled-coil pocket of the soluble model is indicative of binding of the candidate drug to the N-helix coiled-coil pocket and demonstrates that the candidate drug is a drug which binds the N-helix coiled-coil pocket. If the labeled candidate drug is detected on the fusion protein, the candidate drug is a drug which binds the N-helix coiled-coil cavity.

In another embodiment of the method of identifying a drug that binds the N-helix coiled-coil pocket of the HIV gp41, a soluble model that presents the pocket in such a manner that it is available for binding by a drug is combined with a candidate drug and whether binding of the candidate drug with the N-helix coiled-coil of the soluble model occurs is determined. If binding occurs, the candidate drug is a drug which binds the pocket. Here, too, a competitive assay format can be used. The components of the competition assay (e.g., IQN17 and a D-peptide) can be labeled, with any of a variety of detectable labels, including fluorophore/quencher combinations. The candidate drug can be labeled, as described above, with any of a variety of detectable labels. The components of the soluble model (fusion protein) used in this embodiment and the competing moiety which is used in a competitive assay format can also be as described above.

The present disclosure also relates to a method of producing a drug that binds the N-helix coiled-coil pocket of HIV gp41. In one embodiment, the method is carried out as follows: A soluble model that presents the N-helix coiled-coil pocket of HIV gp41 or a fusion protein which comprises a soluble, trimeric coiled-coil is combined with a candidate drug to be assessed for its ability to bind the N-helix coiled-coil pocket of HIV gp41 and inhibit entry into cells, under conditions appropriate for presentation of the HIV gp41 pocket for binding by a drug. Whether the candidate drug binds the HIV gp41 pocket is determined, wherein if binding of the candidate drug to the N-helix coiled-coil pocket of HIV gp41 occurs, the candidate drug is a drug which binds the N-helix coiled-coil cavity of HIV gp41. In this embodiment, the fusion protein comprises a soluble, trimeric coiled-coil and a sufficient portion of the N-peptide of HIV gp41 to include the HIV gp41 N-helix coiled-coil pocket IQN17, described herein, can be used in this method; the D enantiomer of IQN17 can also be used (e.g., in mirror-image phage applications). The ability of the drug produced to inhibit HIV entry into cells is assessed, for example, in a syncytium assay and/or an infectivity assay, as described herein. It can be further assessed in an appropriate animal model or in humans.

Also disclosed herein is a method of producing a drug that binds the N-helix coiled-coil pocket of HIV gp41. The method comprises: producing or obtaining a soluble model of the N-helix coiled-coil pocket of HIV gp41; combining a candidate drug (a molecule or compound) to be assessed for its ability to bind the N-helix coiled-coil pocket of HIV gp41 and the soluble model of the N-helix coiled-coil pocket of HIV gp41 and determining whether the candidate drug binds the N-helix coiled-coil pocket of HIV gp41. If the candidate drug binds the N-helix coiled-coil pocket of HIV gp41, the candidate drug is a drug which binds the N-helix coiled-coil pocket of HIV gp41; as a result, a drug which binds the N-helix coiled-coil cavity of HIV gp41 is produced. The fusion protein used in this embodiment is described herein and can be, for example, IQN17, the D enantiomer of IQN17, or variants thereof. Alternatively, a drug that binds the N-helix coiled-coil pocket of HIV gp41 and inhibits entry of HIV into cells can be produced by a method comprising: producing or obtaining a soluble model of the N-helix coiled-coil pocket of HIV gp41, as described herein; combining the soluble model and a candidate drug to be assessed for its ability to bind the N-helix coiled-coil pocket of HIV gp41; determining whether the candidate drug binds the N-helix coiled-coil pocket of the soluble model (fusion protein), wherein if binding occurs, the candidate drug is a drug which binds the N-helix coiled-coil of HIV gp41; and assessing the ability of the drug which binds the N-helix coiled-coil to inhibit HIV entry into cells, wherein if the drug inhibits HIV entry into cells, it is a drug which binds the N-helix coiled-coil pocket of HIV gp41 and inhibits HIV entry into cells. Its ability to inhibit HIV entry into cells can be assessed in vitro (e.g., in a syncytium assay, an infectivity assay) or in vivo (e.g. in an appropriate animal model or in humans). The soluble model can be a peptide which comprises a soluble, trimeric coiled-coil, such as that of a protein and a sufficient portion of the N-peptide of HIV gp41 to include the HIV gp41 pocket.

Drugs identified or produced by the methods described herein, as well as by other methods, which bind the N-helix coiled-coil pocket of HIV gp41 and inhibit HIV entry into cells are also the subject of this disclosure.

Drugs identified or produced by the methods described herein, as well as by other methods, which bind to more than one N-helix coiled-coil pocket of HIV gp41 and inhibit HIV entry into cells are also the subject of this disclosure. Such drugs can be obtained, for example, by linking two or more pocket-binding molecules (drugs) via an appropriate linker (e.g., a linker of amino acid residues or other chemical moieties) to increase the effectiveness of inhibition. The pocket-binding molecules that are linked can be the same or different. Drugs identified or produced by the methods described herein or by other methods which bind to the N-helix coiled-coil pocket of HIV gp41, in addition to binding to HIV gp120, CD4, CCR5, CXCR4, or a non-pocket region of HIV gp41 are also the subject of this disclosure.

Drugs which inhibit HIV gp41 can also be designed or improved with reference to the X-ray crystal structure of the complex IQN17 and 2K-PIE1, which is presented herein. Alternatively, or in addition, drugs which inhibit HIV gp41 can also be designed or improved with reference to the X-ray crystal structure of free IQN17, presented herein.

Compounds and molecules (drugs) identified as described herein inhibit (partially or totally) entry of HIV into cells, and thus are useful therapeutically in uninfected individuals (humans) and infected individuals (e.g., to prevent or reduce infection in an uninfected individual, to reduce or prevent further infection in an infected individual) and as research reagents both to study the mechanism of gp41-induced membrane fusion and to assess the rate of viral clearance by an individual and as reagents to discover or develop other compounds and molecules (drugs) that inhibit entry of HIV into cells. D-peptides described herein (e.g., D10pep5, D10pep1) have been shown, using the infectivity assay described herein, to inhibit infection of cells. Other D-peptides can be similarly assessed for their ability to inhibit infectivity.

As disclosed above, putative inhibitors can be identified using Fluorescence Resonance Energy Transfer (FRET) to quickly identify interactions. The underlying theory of the techniques is that when two molecules are close in space, i.e., interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

Using methodology well known to those of skill in the art, in combination with various combinatorial libraries, one can isolate and characterize those small molecules which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene2, 3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos.

5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes. The disclosed peptides can be used in a variety of ways as research tools. For example, the disclosed peptides, such as SEQ ID NOS: 1-22 can be used to study gp41, by for example acting as inhibitors of viral entry or of proper folding of the protein.

2. Methods of Inhibiting Viral Entry

Disclosed herein are methods for inhibition of transmission of a virus to a cell, or inhibiting viral entry, comprising exposing the virus to compositions, peptides or multimers as disclosed herein, and thereby inhibiting transmission of the virus to the cell. The virus can be HIV. The peptides or multimers can be in a pharmaceutical composition. Also disclosed are methods of administering a pharmaceutical composition described herein.

In certain embodiments, the methods disclosed herein for inhibition of transmission of a virus to a cell comprise administering a composition comprising at least one D-peptide linked to a potency-enhancing cargo with a polyethylene glycol (PEG) linker. In particular embodiments, the methods comprise administering a composition comprising at least one D-peptide and a potency-enhancing cargo, wherein the at least one D-peptide is at least one of SEQ ID NOS: 1-29, and wherein the potency-enhancing cargo is at least one of a cholesterol, a fatty acid, and an alkane chain. In one such embodiment, the methods comprise administering a composition comprising chol-PEG$_{24}$-PIE12.

In other embodiments, the methods disclosed herein for inhibition of transmission of a virus to a cell comprise administering a composition comprising at least three D-peptides linked to a multimer scaffold, wherein the at least three D-peptides are linked to the multimer scaffold with a PEG linker. In certain such embodiments, the methods comprise administering a composition comprising at least three D-peptides linked to a multimer scaffold, wherein the at least three D-peptides comprise at least one of SEQ ID NOS: 1-29. In one such embodiment, the methods comprise administering a composition comprising PEG$_4$-PIE12-trimer.

In some embodiments, the methods disclosed herein for inhibition of transmission of a virus to a cell comprise administering a composition comprising at least three D-peptides and at least one potency-enhancing cargo linked to a multimer scaffold. In some particular embodiments, the methods comprise administering a composition comprising at least three D-peptides and at least one potency-enhancing cargo linked to a multimer scaffold, wherein the multimer scaffold is a heterotetrameric scaffold comprising three NHS ester groups and a fourth orthogonal group. In still other embodiments, the methods comprise administering a composition comprising at least three D-peptides and at least one potency-enhancing cargo linked to a multimer scaffold wherein the at least one potency-enhancing group is linked to the multimer scaffold via a fourth orthogonal group with a PEG linker. In some particular embodiments, the methods comprise administering a composition comprising at least three D-peptides and at least one potency-enhancing cargo linked to a multimer scaffold wherein the at least one potency-enhancing group is a cholesterol, a fatty acid, or an alkane chain. In one such embodiment, the methods comprise administering a composition comprising at least one of chol-PEG$_{12}$-PIE12-trimer, chol-PEG$_{16}$-PIE12-trimer, chol-PEG$_{24}$-PIE12-trimer, chol-PEG$_{36}$-PIE12-trimer, chol-PEG$_{57}$-PIE12-trimer, chol-PEG$_{132}$-PIE12-trimer, C8 fatty acid-PEG$_{24}$-PIE12-trimer, C16 fatty acid-PEG$_{24}$-PIE12-trimer, C18 fatty acid-PEG$_{24}$-PIE12-trimer, C8 alkane-PEG$_{24}$-PIE12-trimer, C16 alkane-PEG$_{24}$-PIE12-trimer, and C18 alkane-PEG$_{24}$-PIE12-trimer.

The methods disclosed herein can be used in conjunction with other viral therapies or antiviral agents. One of more of these antiviral agents can be used, and they can be administered before, during, or after treatment with the compositions disclosed herein. For example, in ongoing therapy, the subject can be administered the compositions comprised herein simultaneously with other treatments, meaning they can be administered about 48 hours, 24 hours, 12 hours, 8 hours, 4 hours, 2 hours, 1 hour, 30 minutes, 20 minutes, 10 minutes, 5 minutes, or one minute before treatment with the disclosed compositions. Other methods of treatment can also be administered before treatment with the compositions disclosed herein. By "before treatment" is meant that another form of treatment was given and then stopped before the current therapy was administered, or could be given immediately before, then administered again afterwards. In this case, the other methods of antiviral therapy can be administered years, months, weeks, days, hours, or minutes in advance. Other methods of treatment can also be administered after treatment with the compositions disclosed herein. By "after treatment" is meant that another form of treatment is administered after the current therapy was administered, or could be given before, then administered again afterwards. This additional antiviral treatment could be given years, months, weeks, days, hours, or minutes after the current therapy is given.

The further antiviral agent or agents can be selected from the group consisting of a viral replication inhibitor, a viral protease inhibitor, a viral reverse transcriptase inhibitor, a viral entry inhibitor, a viral integrase inhibitor, a viral Rev inhibitor, a viral Tat inhibitor, a viral Nef inhibitor, a viral Vpr inhibitor, a viral Vpu inhibitor, and a viral Vif inhibitor.

Further examples of antiviral compounds include, but are not limited to, amantadine, rimantadine, zanamavir and oseltamavir (Tamiflu) for the treatment of flu and its associated symptoms. Antiviral compounds useful in the treatment of HIV include Combivir® (lamivudine-zidovudine), CRIXIVAN® (indinavir), EMTRIVA® (emtricitabine), EPIVIR® (lamivudine), FORTOVASE® (saquinavir-sg), HIVID® (zalcitabine), INVIRASE® (saquinavir-hg), KALETRA® (lopinavir-ritonavir), LEXIVA™ (fosamprenavir), NORVIR® (ritonavir), RITROVIR® (zidovudine) SUSTIVA® (efavirenz), VIDEX EC® (didanosine), VIDEX® (didanosine), VIRACEPT® (nelfinavir) VIRAIVIUNE® (nevirapine), ZERIT® (stavudine), ZIAGEN® (abacavir), FUZEON® (enfuvirtide) RESCRIPTOR® (delavirdine), REYATAZ® (atazanavir), TRIZIVIR® (abacavir-lamivudine-zidovudine) VIREAD® (tenofovir disoproxil fumarate) ISENTRESS® (raltegravir), SELZENTRY® (maraviroc), and AGENERASE® (amprenavir).

Examples of viral infections include but are not limited to, infections caused by all RNA viruses (including negative stranded RNA viruses, positive stranded RNA viruses, double stranded RNA viruses and retroviruses) and DNA viruses. Examples of viruses include, but are not limited to, HIV (including HIV-1 and HIV-2), parvovirus, papillomaviruses, measles, filovirus (for example, Ebola, Marburg), SARS (severe acute respiratory syndrome) virus, hantaviruses, influenza viruses (e.g., influenza A, B and C viruses), hepatitis viruses A to G, caliciviruses, astroviruses, rotaviruses, reovirus, coronaviruses, (for example, human respiratory coronavirus and SARS coronavirus (SARS-CoV)), picornaviruses, (for example, human rhinovirus and enterovirus), Ebola virus, human herpesvirus (such as, HSV-1-9, including zoster, Epstein-Barr, and human cytomegalovirus), foot and mouth disease virus, human adenovirus, adeno-associated virus, respiratory syncytial virus (RSV), smallpox virus (variola), cowpox, monkey pox, vaccinia, polio, viral meningitis and hantaviruses.

For animals, viruses include, but are not limited to, the animal counterpart to any above listed human virus, avian influenza (for example, strains H5N1, H5N2, H7N1, H7N7 and H9N2), and animal retroviruses, such as simian immunodeficiency virus, avian immunodeficiency virus, pseudocowpox, bovine immunodeficiency virus, feline immunodeficiency virus, equine infectious anemia virus, caprine arthritis encephalitis virus and visna virus.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Inhibitory D-Peptides a) Peptide Synthesis

In this example, all synthesized peptides were capped with N-terminal acetyl and C-terminal amide groups, and their masses confirmed by MALDI-TOF. Crude peptides were purified by reverse-phase HPLC (RP-HPLC) on a C18 column (Vydac) and lyophilized. D-peptide inhibitors were oxidized at (≤0.4 mg/mL) overnight at 37° C. in 50 mM Tris, pH 8.0, 2% DMSO, and repurified using RP-HPLC.

PEG-(PIE7)$_2$ was made by incubating PIE7 (~2 mM) with freshly prepared crosslinker (Bis-dPEG$_9$™ NHS ester, Quanta BioDesign, #10246) at a 1:0.6 (peptide:PEG) molar ratio in 50 mM NaHPO$_4$, pH 7.0, for 2 h at RT. PEG-(PIE2-AAA)$_2$ was made using a similar protocol. PEG-PIE7 was made using a similar protocol with NHS-m-dPEG™ (Quanta BioDesign, #10260) at a 1:2 (peptide:PEG) molar ratio.

b) Viral Infectivity Assay:

This study included the use of the HIV HXB2 strain and the HIV JRFL strain. Viral infectivity was measured essentially as previously described (Hamburger 2005) with several modifications. 8 µg/mL DEAE-Dextran was used as a fusion enhancer in all assays.

Media was changed 22-26 h following infection. IC$_{50}$ values were calculated by fitting normalized data to the following equation: y=1/(1+[inhibitor]/IC$_{50}$). Fits were weighted by the absolute s.e.m. from quadruplicate points with the minimum allowable error set to 1%. Samples requiring DMSO for solubility (D10-p5, PEG-(PIE2-AAA) 2, PEG-(PIE7)2, and PEG-PIE7) were tested at 1% final DMSO concentration and normalized to an uninhibited control containing 1% DMSO. The following reagents were obtained through the AIDS Research and Reference Reagent Program, Division of AIDS, NIAID, TAK779 and T-20 (FUZEON®) from NIAID and Roche, respectively.

c) Results and Discussion

The peptides discussed herein are D-peptides that are pocket-specific inhibitors of entry (PIE). Examples include: PIE7-GK (GACDYPEWQWLCAAGK, SEQ ID NO: 23). This peptide is the same as PIE7, except that the Lys has been moved to the C-terminus. The move results in slightly enhanced potency and allows for the crosslinking of peptides via their C-termini.

PIE7-GKK (GACDYPEWQWLCAAGKK, SEQ ID NO: 24). This is a double Lys variant of PIE7-GK, and serves as a central peptide in trimeric PIE7 (the central PIE7-GKK is connected to two flanking PIE7-GK peptides). These connections are all via the C-terminus.

K-PIE7-GK (KGACDYPEWQWLCAAGK, SEQ ID NO: 25). This double Lys variant of PIE7-GK serves as a central peptide in trimeric PIE7 (the central K-PIE7-GK is connected to two flanking peptides—PIE7-GK and PIE7). These connections link the N- to C-termini of neighboring peptides.

PIE7-GK-PEG$_4$: (PIE7-GK with PEG$_4$ attached). This peptide is a control to determine how well PEG additions are tolerated on the C-terminus of the D-peptides. From this peptide, it was learned that such additions are well tolerated.

The following group of new peptides arose from optimization of the flanking sequences:

```
                             (SEQ ID NO: 26)
HPCDYPEWQWLCELGK (SEQ ID NO: 27)
HPCDYPEWQWLCKLGK (SEQ ID NO: 28)
HPCDYPEWQWLCRLGK (SEQ ID NO: 29)
HACDYPEWQWLCELGK
```

The multimers disclosed herein were found to have avidity. More particularly, the dimeric inhibitors PEG-(PIE2-AAA)$_2$ and PEG-(PIE7)$_2$ have IC$_{50s}$ of 21 nM and 1.9 nM (Table 2), respectively. These values represent a ~70- and ~325-fold improvement over the corresponding monomers. These data also indicate that modest improvements in the potency of monomeric inhibitors are magnified by avidity in the dimer, as also observed in the phage display. The potency of PEG-(PIE7)$_2$ is comparable to FUZEON® (Table 2). The improved potency of the dimers cannot be attributed to an interaction of the PEG with virus, cells, or the D-peptide, but is a genuine avidity effect caused by two D-peptides binding to the N-trimer.

TABLE 2

Inhibitory Potency of D-peptides against HXB2 and JRFL Pseudovirion Entry

| Sample | IC$_{50}$ (nM)† (HXB2) | IC$_{50}$ (nM) (JRFL) |
|---|---|---|
| D10-p5 | 9.5 | >25,000 |
| 2K-PIE1 | 2.2 | >100,000 |
| 2K-PIE2 | 2.6 | ND |
| PIE2-AAA | 1.4 | ND |
| PIE2 | 1.3 | 66,000 |
| PIE8 | 1.7 | ~110,000 |
| PIE7 | 620 | 24000 |
| PIE7-GK | 390 | 15800 |

TABLE 2-continued

Inhibitory Potency of D-peptides against HXB2 and JRFL Pseudovirion Entry

| Sample | IC$_{50}$ (nM)† (HXB2) | IC$_{50}$ (nM) (JRFL) |
|---|---|---|
| PIE7-GKK | 380 | 19100 |
| K-PIE7-GK | ND | 14800 |
| PIE7-GK-PEG$_4$ | 350 | 13100 |
| PIE12 | 37 | 578 |
| PIE13 | 41 | 1470 |
| PIE14 | 33 | 1050 |
| PIE15 | 67 | 1450 |
| N$_9$N(PIE7)$_2$ | 1.9 | 2300 |
| N$_9$C(PIE7)$_2$ | 0.33 | 310 |
| C$_9$C(PIE7-GK)$_2$ | 0.35 | 220 |
| N$_5$N(PIE7)$_2$ | 1.1 | 1410 |
| N$_5$C(PIE7)$_2$ | 0.58 | 300 |
| C$_5$C(PIE7-GK)$_2$ | 0.36 | 200 |
| N$_0$N(PIE7)$_2$ | 0.80 | 1090 |
| N$_0$C(PIE7)$_2$ | 0.53 | 400 |
| C$_0$C(PIE12)$_2$ | 0.29 | 14 |
| PEG5-(PIE13)$_2$ | ND | 15 |
| N$_9$N(PIE7)$_3$ | 0.25 | 220 |
| C$_5$C(PIE7-GK)$_3$ | 0.13 | 6.7 |
| C$_5$C(PIE12)$_3$ | ND | 2.8 |
| C$_0$C(PIE7-GK)$_3$ | 0.12 | 16.1 |
| PIE7-GK long claw | 0.12 | 20.6 |
| PIE7-GK short claw | 0.23 | 86.6 |
| C37 | 1.4 | 13.0 |
| FUZEON ® | 3.7 | 5.0 |

†IC$_{50}$ s.e.m. is <20% and K$_D$ s.e.m. is <5% for duplicate assays for all values
ND = Not determined The use of the peptides disclosed herein have significant effects across HIV clades utilizing the same PIE construct. For example, PIE12-trimer showed IC$_{50}$ of less than 10 nM against replication competent HIV strains that cover envelope subtypes A, B, C, D, E, F, and G while maintaining no toxicity for dosage up to 10 μM (Table 3). By comparison, the IC$_{50}$ of FUZEON® was less than the 10 nM level in only three strains (clades B and E only) and in those instances was between 6 and 100 times less potent than the PIE12-trimer. In fact, FUZEON® had >100-fold less inhibition for HIV subtype A viruses, from 6- to 250-fold less inhibition for subtype B viruses, ~60-fold less inhibition for subtype C viruses, between 40- and 100-fold less inhibition for subtype D viruses, 25- to 150-fold less inhibition for subtype F strains, and 20 to 100-fold less inhibition for subtype G strains.

TABLE 3

Inhibitory breadth against replication competent virus and PBMC target cells.

| HIV-1 Isolate | Envelope Subtype | IC50 PIE12 trimer | (nM) Fuzeon |
|---|---|---|---|
| IIIB | B | 0.78 | 28.3 |
| Ba-L | B | 0.27 | 19.7 |
| JR-CSF | B | 0.08 | 7.03 |
| JR-FL | B | 0.26 | 1.65 |
| 92UG029 | A | 0.69 | 191 |
| 92UG037 | A | 0.21 | 41.45 |
| 93IN101 | C | 0.38 | 22.4 |
| 92BR025 | C | 5.19 | 305 |
| 92UG001 | D | 4.45 | 182 |
| 92UG046 | D | 1.2 | 130 |
| CMU02 | AE | 0.35 | 43.8 |
| 93TH073 | E | 0.84 | 198 |
| CMU06 | E | 0.38 | 5.65 |
| 93BR019 | BF | 4.72 | >1,000 |
| 93BR020 | F | 0.37 | 58.5 |
| 93BR029 | F | 0.79 | 18.6 |
| G3 | G | 1.21 | 23.3 |
| RU570 | G | 0.36 | 37 |

No toxicity observed up to 10 μM

Example 2

Cholesterol Cargo a) Synthesis of D-peptides with Cholesterol Cargo

D-peptide monomers with cholesterol potency-enhancing cargo were made using heterobifunctional PEG NHS ester/maleimide crosslinkers to conjugate thiocholesterol (cholesterol with a thiol replacing its hydroxyl group) to the terminal Lys of PIE12-GK (where PEG is polyethylene glycol and NHS is N-Hydroxysuccinimide; Quanta BioDesign, catalog #10994). For synthesis of D-peptide trimers with potency-enhancing cholesterol cargo, PIE12-GK (11 mM) was reacted with Fmoc-N-amido-dPEG$_4$-NHS ester at a 1.05:1 (peptide:PEG) molar ratio in dimethylacetamide buffered by triethylamine (TEA, 200 mM) for 40 minutes at room temperature (RT). The product was purified by C18 reverse phase (RP) HPLC and lyophilized. The Fmoc protecting group was then removed by resuspending the product in 20% piperidine (in dimethylacetamide), and the deprotected product was purified by C18 RP-HPLC. This material (PIE12-GK-PEG4-NH2, 10 mM) was reacted with Mal-dPEG$_{12}$-Tris(NHS)$_3$ (Quanta BioDesign, catalog #10676) at a 3.2:1 (peptide:scaffold) molar ratio in dimethylacetamide buffered by 200 mM triethylamine at RT for 40 min. Reaction progress was monitored by RP-HPLC. To this reaction, thiocholesterol (25 mM stock solution in 90% Dimethylacetamide, 10% chloroform, 200 mM TEA) was added to a final concentration of 4 mM. The final product was purified by RP-HPLC and lyophilized, and its identity confirmed by mass spectroscopy (mass 8061.81 Da).

Lengths of the three NHS ester arms (used for attaching PIEs) can be modified by using Fmoc-N-amido-dPEGx-NHS ester, where x can range from 1 to 36 (as discrete PEG lengths) or longer (as polydisperse PEGs with a specified average length). PEGs can be synthesized as continuous molecules or can be stitched together using smaller PEGs. For example, reacting the maleimide group on the PEG$_{12}$ arm with a cysteine residue converts the maleimide to a primary amine, which can be used with NHS ester PEG-maleimide to extend the length of the PEG arm and restore a maleimide group to its terminus. This was the strategy used to make PEGs designated with an asterisk in Table 4.

b) Results

Table 4 shows the results of conjugating the cholesterol cargo to PIE12 monomer or PIE12-trimer on the inhibition of membrane entry by two HIV strains, HXB2 and JRFL. For the PIE12 monomer, addition of chol-PEG$_2$ resulted in a significantly weaker inhibitor, while a PEG$_{12}$ linker provided a nearly 3-fold improvement in potency. Unexpectedly, a PEG$_{24}$ linker provided a ~100-fold boost in potency for the PIE12 monomer. Application of PEG$_{24}$ to PIE12-trimer resulted in an even greater improvement in potency (~250-fold). In Table 4, the asterisks refer to PEG chains that were assembled by connecting two smaller PEG chains (e.g., PEG$_{24}$*=two PEG12 chains connected in series).

TABLE 4

Inhibitory Potency of D-peptides against HXB2 and JRFL Pseudovirion Entry with cholesterol potency-enhancing cargo.

| Sample | IC50 (nM) (HXB2) | IC50 (nM) (JRFL) | IC50 (nM) E560K/ V570IHXB2 | IC50 (nM) Q577R HXB2 |
|---|---|---|---|---|
| PIE12 | 37 | 580 | 240 | 10200 |
| Chol-PEG$_2$-PIE12 (monomer) | 58 | | | |
| Chol-PEG$_{12}$-PIE12(monomer) | 11 | 200 | | |
| Chol-PEG$_{24}$-PIE12 (monomer) | 0.40 | | | |
| C5C-PIE12-trimer | 0.33 | 2.8 | 0.84 | 2960 |
| Chol-PEG$_{12}$-PIE12-trimer | | 0.044 | | |
| Chol-PEG$_{16}$*-PIE12-trimer | | 0.020 | | |
| Chol-PEG$_{24}$*-PIE12-trimer | | 0.011 | | |
| Chol-PEG$_{36}$*-PIE12-trimer | 0.0054 | 0.011 | 0.0045 | 2.7 |
| Chol-PEG$_{24}$-PIE12-trimer | | 0.0142 | | |

Figure 2:
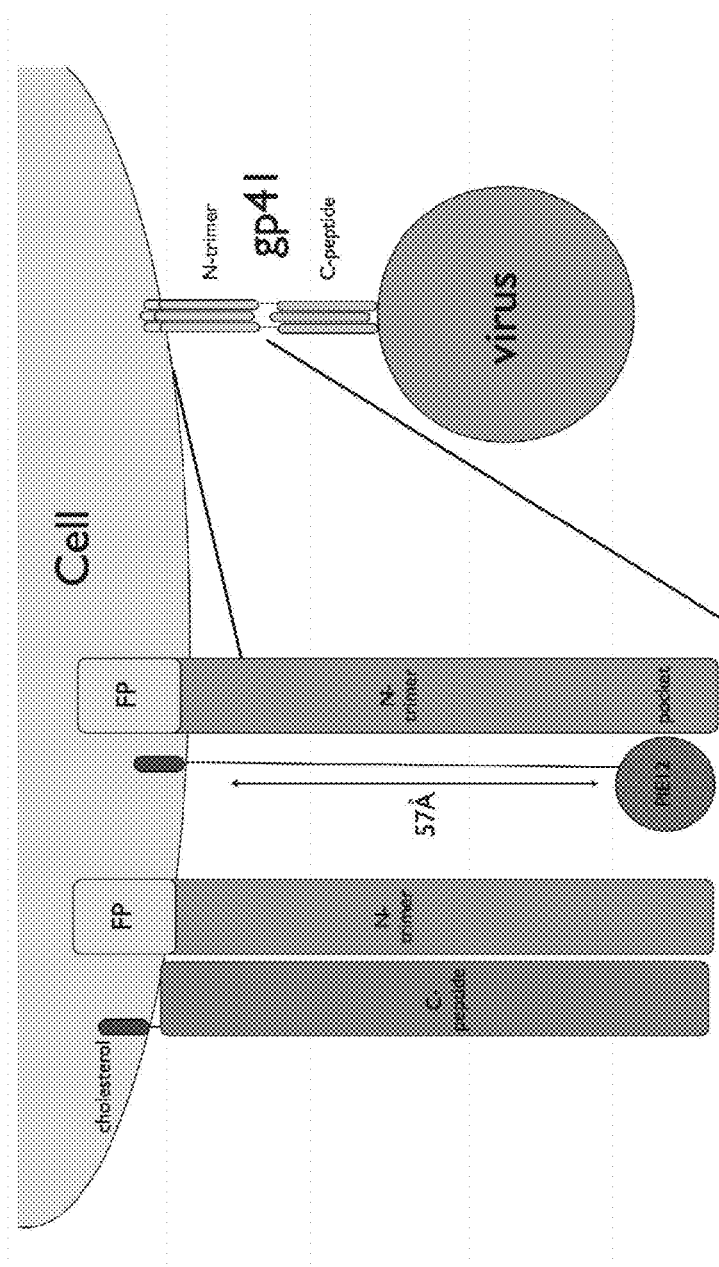
FIG. 2 shows an estimated distance between the N-trimer pocket region (D-peptide binding site) and the target cell membrane.

As shown in FIG. 1 and FIG. 2, the gp41 pocket region is approximately ~57 Å to ~60 Å away from the cell surface. Therefore, a relatively long linker may be used to bridge this distance between the membrane and a PIE (e.g., PIE12 in FIG. 2). Prior to the testing conducted herein, it was thought that such a long linker arm could reduce the local concentrating effect of cholesterol. Surprisingly, this is not the case. As seen in Table 4, cholesterol connected to monomeric or trimeric PIE12 via long PEG arms (e.g., 24 or 36 units, predicted to be long enough to bridge 57 Å) produces an inhibitor with >100-fold improved potency.

Table 4 also shows two resistance mutations discovered against PIE7-dimer (E560K/V570I) and PIE12-trimer (Q577R). The resistance mutations have a similar relative effect on cholesterol linked PIE12-trimers, but the much improved potency of the cholesterol-linked peptides allows these peptides to maintain good inhibitory activity even against these resistant strains.

Example 3

Modular Homotrimeric Scaffold

A homotrimeric scaffold was designed containing three NHS ester arms (trimeric trimethoylester triNHS) for conjugation to D-peptides in a single-pot reaction. PEG linkers of various lengths can be appended to the D-peptide, allowing for the simple production of D-peptide-trimers with varying PEG lengths.

a) Peptide Synthesis

Peptides were synthesized using a PTI PS3 peptide synthesizer or by RS Synthesis to generate either PIE12-GK or AHP-PIE12-GK (lacks two N-terminal residues, D-His and D-Pro) (Welch, 2007 and 2010). PIE12-dPEG$_{4/5}$-NH$_2$ (the precursor to PIE12-trimer synthesis) was synthesized as follows: PIE12-GK (10 mM in dimethylacetamide, DMAC) was reacted with 250 mM Fmoc-N-amido-dPEG$_{4/5}$-NHS ester (Quanta BioDesign 10994 and 10053) in dry DMAC (Acros Organics, septa sealed with molecular sieves) at a 1:1 molar ratio buffered by triethylamine (200 mM, pH 7.5) for 60 minutes at RT. This reaction was quenched by addition of acetic acid to 5% and purified by reverse-phase HPLC (water/acetonitrile gradient in 0.1% TFA) on a Waters BEH X-Bridge 10 µm, 300 Å C$_{18}$ column (RP-HPLC). Purified product was lyophilized, then resuspended in 20% piperidine in DMAC for 20 minutes to remove Fmoc and produce PIE12-PEG$_{4/5}$-NH$_2$, which was then purified by RP-HPLC.

b) Trimer Synthesis

PIE12-PEG$_{4/5}$-NH$_2$ (10 mM) was reacted with 250 mM trimethylolethane-triNHS ester (FIG. 3a, Quanta BioDesign 10674) in DMAC at a 3.3:1 (peptide/scaffold) ratio in DMAC buffered by triethylamine (200 mM, pH 7.5) for 60 minutes at RT. Product was purified by RP-HPLC. All masses were confirmed by ESI-MS (AB Sciex API-3000).

Cholesterol-PIE12-trimer and alkyl-PIE12-trimer were synthesized as follows: PIE12-PEG$_4$-NH$_2$ (10 mM) was reacted with Maleimide-PEG$_{12}$-triNHS ester (Quanta BioDesign 10676, 250 mM in DMAC) or Maleimide-PEG$_{24}$-triNHS ester (FIG. 3b, Quanta BioDesign 10680, 250 mM in DMAC) at a 3.3:1 (peptide/scaffold) ratio in DMAC buffered by triethylamine (200 mM, pH 7.5) for 45 minutes at RT, each using a carbon-centered multimer scaffold. Thiocholesterol (Sigma Aldrich, 136115, 250 mM in chloroform), 1-octanethiol (Sigma-Aldrich 471836), 1-Hexadecanethiol (Sigma-Aldrich 52270) or 1-octadecanethiol (Sigma Aldrich 01858) were then added to a final concentration of 4.5 mM and reacted for an additional 60 minutes. For PEG$_{16}$, PIE12-PEG$_4$-NH$_2$ was first reacted with Mal-PEG$_{12}$-triNHS ester, followed by reaction with D-Cysteine (5 mM) to yield (PIE12-PEG$_4$)$_3$-PEG$_{12}$-Cys. This product was then purified by RP-HPLC before sequential reaction with Maleimide-PEG$_4$-NHS and thiocholesterol under conditions identical to those used to generate chol-PEG$_{24}$-PIE12-timer. PEG$_{36}$, PEG$_{57}$, and PEG$_{132}$-trimer were produced through conjugation of PIE12-PEG$_4$-NH$_2$ to Maleimide-PEG$_{24}$-triNHS ester, followed by addition of D-Cysteine. This intermediate was then conjugated to Mal-PEG$_{12}$-NHS ester (Quanta Biodesign, 10284), Mal-PEG$_{2K}$-NHS ester (Creative PEGWorks, PHB-950, ~45 PEG units), or Mal-PEG$_{5K}$-NHS ester (Creative PEGWorks, PHB-952, ~120 PEG units) to yield Chol-PEG$_{36}$-PIE12-Trimer, Chol-PEG$_{57}$-PIE12-trimer, and Chol-PEG$_{132}$-PIE12-trimer, respectively. The reaction was quenched by addition of acetic acid to 5% before purification by RP-HPLC.

c) Viral Infectivity Assays

Pseudovirion infectivity assays were carried out using HIV HXB2 strain and HIV JRFL strain luciferase reporter pseudovirions (NL4-3 strain) and HOS-CD4-CXCR4 (for HXB2) or HOS-CD4-CCR5 (for JRFL) target cells (Welch, 2007 and 2010). Inhibitors curves were generated using six concentration points measured in quadruplicate, and luciferase counts were normalized to an uninhibited control. Inhibition curves were fit using a standard IC$_{50}$ equation (1−c/(IC$_{50}$+c)) weighting each concentration point by its standard error in KaleidaGraph™ (Synergy Software). Reported IC$_{50}$ values are the average of at least 2 independent assays.

d) Results

Figure 3:
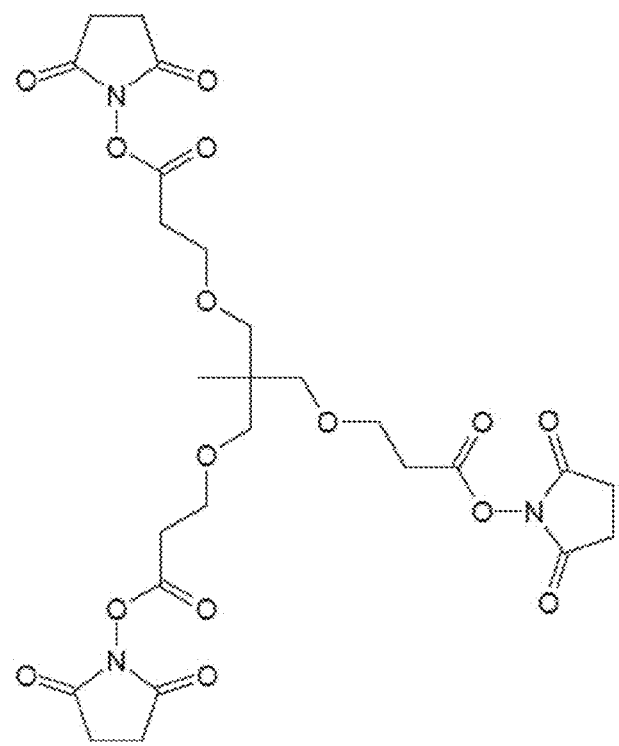
FIG. 3(a) shows one embodiment of a homotrimeric PEG scaffold as disclosed herein, and (b) shows one embodiment of a heterotetrameric PEG scaffold as disclosed herein.
Figure 3:
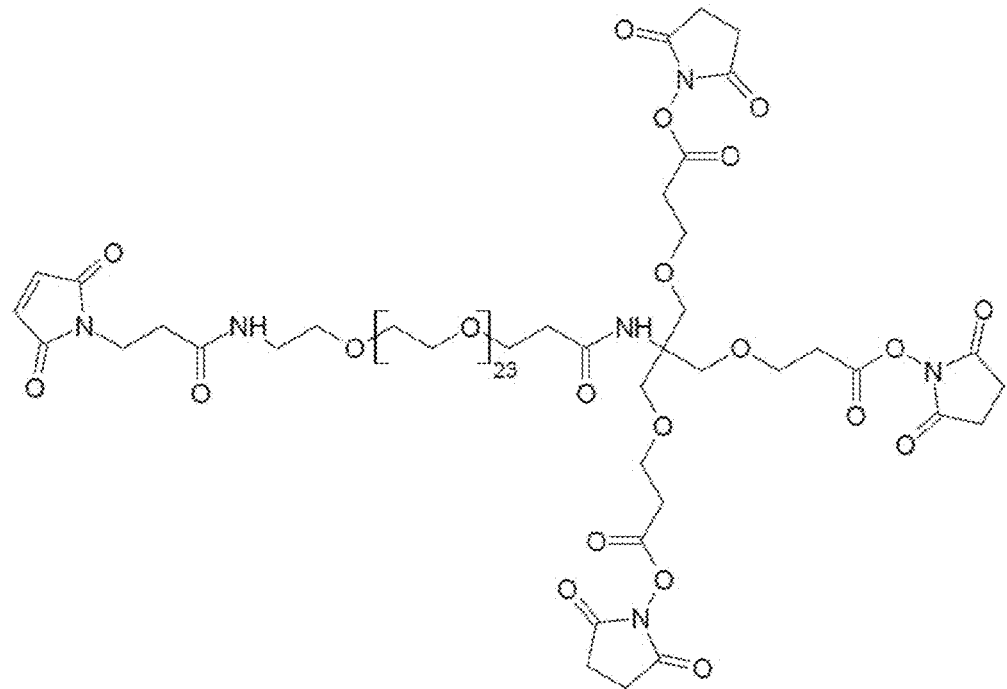

Results show the successful synthesis of D-peptide-trimer using a homotrimer scaffold while also optimizing the PEG linkages between D-peptide monomers. Previously, PIE12-trimer had been synthesized by attaching bis-NHS ester PEG$_5$ spacers to PIE12-GK. After purification, two of these PEGylated monomers were reacted with a central PIE12-GKK monomer (two primary amines) to produce PIE12-trimer (Welch, 2010). This method is cumbersome for large-scale production because it requires the synthesis of two distinct D-peptides and a series of HPLC purifications to assemble the trimer, resulting in low yields. In addition, the PIE12 crystal structure suggested that shorter PEG linkers might adequately bridge the neighboring pockets and improve avidity. To overcome the short comings of this method, a homotrimeric scaffold was designed containing three NHS ester arms for conjugation to D-peptide monomers in a single pot reaction, such as conjugation with PIE12-GK (FIG. 3a). PEG linkers of various lengths can be appended to the PIE12-GK peptide, allowing for the simple production of PIE12-trimers with varying PEG lengths.

PIE12-trimer's estimated sub-fM affinity for the N-trimer makes direct comparative $K_D$ measurements (e.g., by surface plasmon resonance) challenging. Although antiviral potency can be used as a surrogate for affinity, PIE12-trimer's potency plateau can mask even large changes in affinity. To overcome this problem, a PIE12 variant was designed with weakened affinity to allow comparative evaluation of different trimer geometries by measuring inhibitor potency. PIE12's two N-terminal residues make important contacts with the N-trimer and it was reasoned that deletion of these residues (D-His and D-Pro) would significantly reduce binding affinity without disrupting the overall orientation of PIE12 binding to the gp41 pocket or the local structure at the C-terminal PEG linkage site. ΔHP-PIE12 is 84-fold less potent than PIE12 (Table 5). In the context of the homotrimeric scaffold, ΔHP-PIE12 connected via $PEG_5$ linkers has an $IC_{50}$ of 380 nM against HXB2 (a standard lab-adapted strain) and is therefore well outside of the potency plateau (~500 pM for HXB2). Using ΔHP-PIE12-trimer, changes could be detected in potency due to linker changes that subtly alter affinity.

TABLE 5

| D-peptide Inhibition data | | |
|---|---|---|
| | $IC_{50}$ (nM) | |
| Inhibitor | HXB2 | JRFL |
| PIE12* | 37 ± 2.3 | 580 ± 21.4 |
| ΔHP-PIE12 | 3100 ± 783 | nd |
| Chol-$PEG_2$-PIE12-monomer | 69 ± 11 | nd |
| Chol-$PEG_{12}$-PIE12-monomer | 12 ± 3.6 | nd |
| Chol-$PEG_{24}$-PIE12-monomer | 0.64 ± 0.25 | nd |
| C34 | 1.4 ± 0.3 | 13.4 ± 0.1 |
| C34-$PEG_2$-Chol | 0.044 ± 0.0004 | 0.05 ± 0.01 |
| C34-$PEG_{11}$-Chol | 0.021 ± 0.0014 | 0.024 ± 0.005 |
| C34-$PEG_{80}$-Chol | 0.022 ± 0.0004 | 0.1 ± 0.045 |
| $PEG_4$-ΔHP-PIE12-trimer | 300 ± 7.2 | nd |
| $PEG_5$-ΔHP-PIE12-trimer | 380 ± 13 | nd |
| $PEG_4$-PIE12-trimer | 0.72 ± 0.04 | 2.1 ± 0.28 |
| Chol-$PEG_{12}$-PIE12-trimer | 0.052 ± 0.02 | 0.06 ± 0.004 |
| Chol-$PEG_{16}$-PIE12-trimer | 0.02 ± 0.002 | 0.017 ± 0.0002 |
| Chol-$PEG_{24}$-PIE12-trimer | 0.013 ± 0.0013 | 0.019 ± 0.003 |
| Chol-$PEG_{36}$-PIE12-trimer | 0.011 ± 0.0015 | 0.015 ± 0.005 |
| Chol-$PEG_{57}$-PIE12-trimer | 0.007 ± 0.0013 | 0.013 ± 0.003 |
| Chol-$PEG_{132}$-PIE12-trimer | 0.012 ± 0.0015 | 0.025 ± 0.002 |
| C8-$PEG_{24}$-PIE12-trimer | 0.42 ± 0.01 | nd |
| C16-$PEG_{24}$-PIE12-trimer | 0.09 ± 0.014 | 0.11 ± 0.012 |
| C18-$PEG_{24}$-PIE12-trimer | 0.054 ± 0.018 | 0.087 ± 0.012 |

Antiviral potency against HXB2 and JRFL HIV-1 strains (*from 20).

Example 4

Modular Heterotetrameric Scaffold and PEG Linker Optimization

To enable the conjugation of potency-enhancing cargo groups to PIE12-trimer, a heterotetrameric scaffold was designed. The heterotetrameric scaffold comprised three shorter PEG arms with NHS ester groups, for addition of PIE12-$PEG_4$-$NH_2$, a carbon center, and a fourth PEG arm of variable length functionalized with maleimide, an orthogonal reactive group, for the addition of potency-enhancing cargoes (i.e. pharmacokinetic-enhancing and/or membrane-localizing cargoes (FIG. 3*b*).

One of the potency-enhancing cargoes studied for the heterotetrameric scaffold was cholesterol. As disclosed herein, a consideration for using a cholesterol cargo with PIE12 D-peptide is that while the N-terminus of the C-peptide lies immediately adjacent to the membrane, PIE12 targets a pocket that is ~60 Å from the cell membrane (see, e.g. FIG. 1). Flexible PEG linkers of varying lengths were used to span this distance. $PEG_{12}$ is sufficiently long if stretched taut, but PEG typically assumes an average length approximately half of its fully stretched distance.

To study the potency effects of cholesterol (chol) conjugation to a D-peptide, and to optimize the length of the PEG linker between chol and a D-peptide, monomeric PIE12 was used, which is not in a potency plateau and therefore should be a sensitive reporter for optimal PEG linker length. Chol-$PEG_x$-PIE12 conjugates were generated using heterobifunctional $PEG_2$, $PEG_{12}$, and $PEG_{24}$ NHS ester/maleimide crosslinkers to conjugate thiocholesterol (cholesterol with a thiol replacing its hydroxyl group) to PIE12's C-terminal Lys (its only primary amine). It was observed that the chol-$PEG_2$-PIE12 conjugate was too short to bridge the membrane-to-pocket distance and caused a two-fold loss of potency (HXB2 strain) compared to unconjugated PIE12 (Table 5). In contrast, chol-$PEG_{12}$-PIE12 shows 3-fold improved potency, while chol-$PEG_{24}$-PIE12 provided an even greater 58-fold increase in potency compared to PIE12 alone (Table 5).

For comparison, C-peptide (C34) cholesterol conjugates of varying lengths were synthesized (Table 5). Results showed a ~40-fold improved potency using a short $PEG_2$ linker, but surprisingly, a longer linker ($PEG_{11}$) provides an additional 2-fold improvement in potency, and a much longer linker ($PEG_{80}$) maintains the same potency (HXB2 strain). A similar pattern is seen with the JRFL strain, but with significant attenuation at very long PEG linker lengths (4-fold worse than the optimal PEG length).

Based on these potency gains, PIE12-trimer was conjugated to cholesterol using the heterotetrameric scaffold as disclosed herein. Using the optimal $PEG_4$ linker determined earlier for the three NHS ester (PIE12) arms, chol-PIE12-trimers were synthesized with a variety of fourth arm (maleimide) lengths to confirm the relationship between PEG length and potency observed with the monomer. This sensitivity was expected because membrane localization affects the association rate rather than changing affinity (masked by the resistance capacitor). The length of the fourth arm was varied from 12 to 132 PEG units, covering a distance range of ~60 to ~480 Å (fully-extended).

Cholesterol conjugation dramatically improved $PEG_4$-PIE12-trimer potency against both HXB2 and JRFL entry (up to 160-fold, Table 5). Comparison of varying $4^{th}$ arm lengths in chol-PIE12-trimer shows that inhibitor potency varies modestly in an optimal range between $PEG_{24}$ and $PEG_{57}$. As shown in FIG. 4*a*, a shorter $PEG_{12}$ linker is less potent than $PEG_{24}$ and $PEG_{36}$ linkers. Only a slight decrease in potency is observed with the longest ($PEG_{132}$) linker (not shown). The chol-$PEG_{24}$-PIE12-trimer was chosen for further study due to its ease of synthesis and the availability of monodisperse $PEG_{24}$. Furthermore, a monodisperse $PEG_{24}$ scaffold may ease preclinical studies of chol-PIE12-trimer purity, metabolism, pharmacokinetics, and stability. Importantly, cholesterol conjugates retain high (mM) aqueous solubility.

Figure 4:
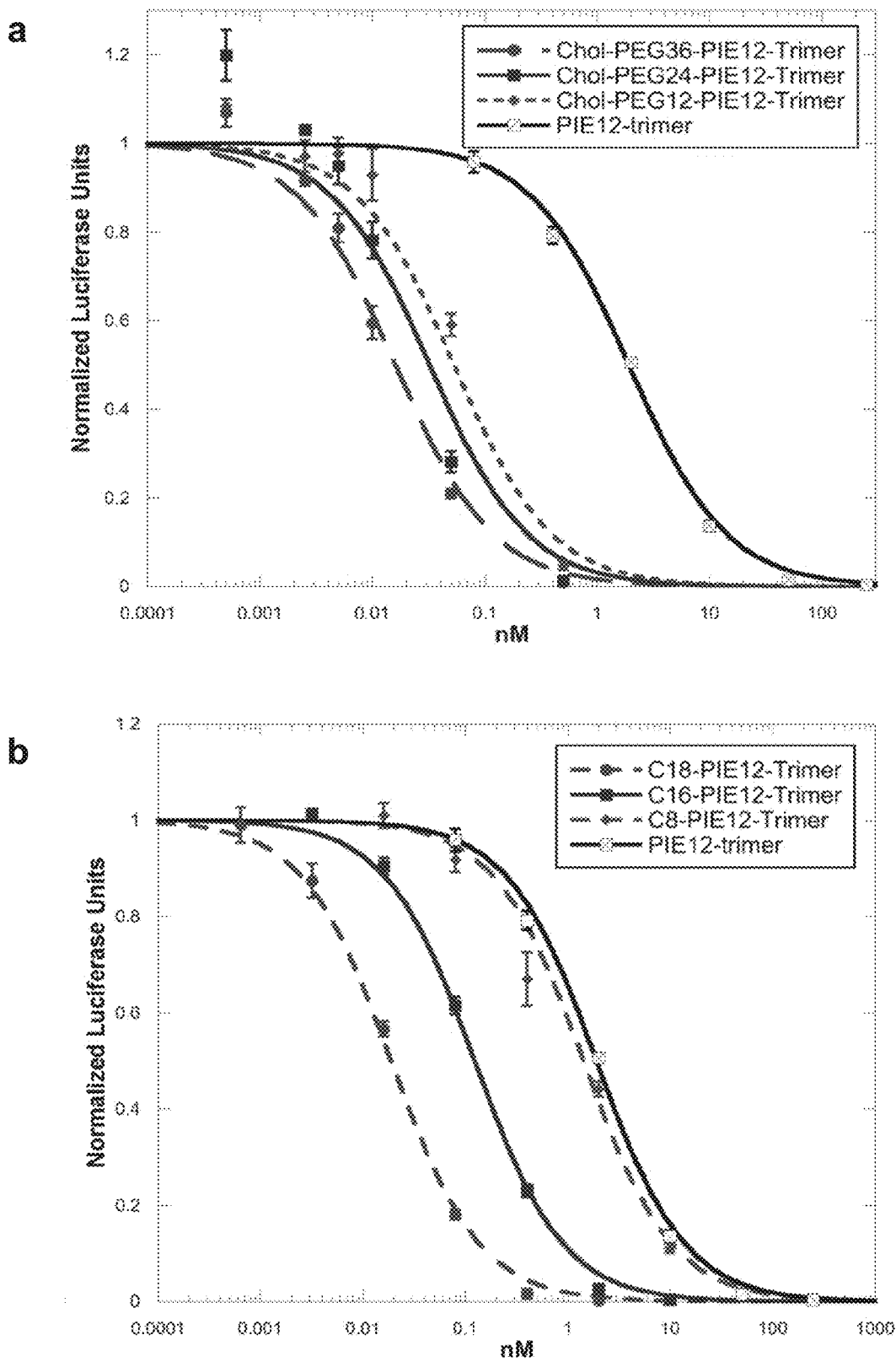
FIG. 4(a) shows the observed effects of the PEG linker length on chol-PIE12-trimer potency, and (b) shows the observed effects of different alkane lengths on C8/C16/C18-PIE12-trimer potency.
Figure 5:
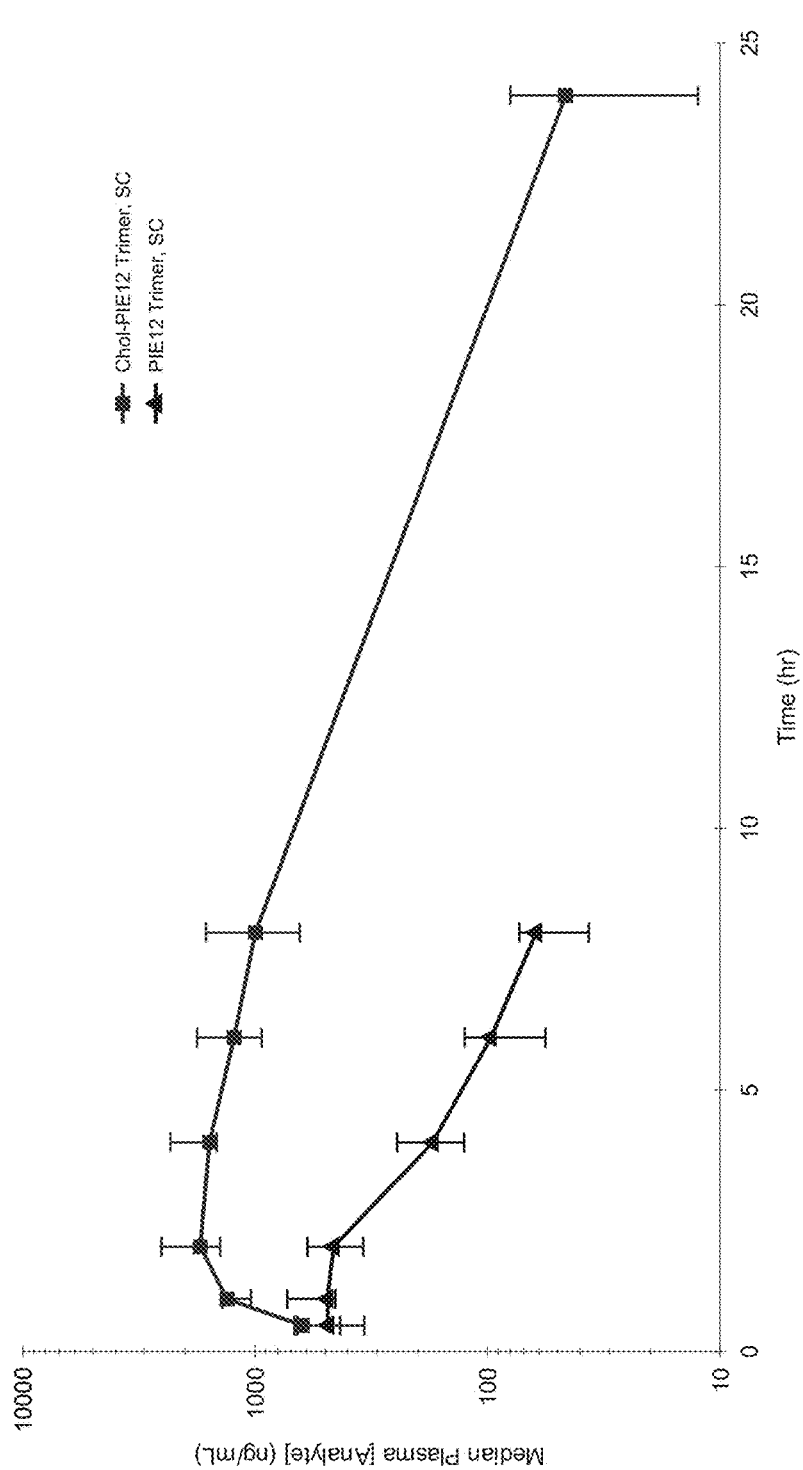
FIG. 5 shows the enhanced pharmacokinetic properties of one embodiment of a chol-PIE12-trimer compared with one embodiment of a PIE12-trimer.

Another strategy for potency enhancement and localizing D-peptide inhibitors to membranes is the use of the heterotetrameric scaffold with fatty acid cargo at the fourth arm. Using the same heterotetramer scaffold synthesis strategy described herein, PIE12-trimers were synthesized and conjugated at the fourth arm to fatty acids cargoes with aliphatic chains of either 8, 16, or 18 carbons (C8/C16/C18 fatty acid-$PEG_{24}$-PIE12-trimer). While C8 fatty acid conjugation has little effect on PIE12-trimer potency, C16 fatty acid and C18 fatty acid both provide gains in potency, though to a lesser degree than seen with cholesterol (FIG. 4b and Table 5). C18 fatty acid-$PEG_{24}$-PIE12-trimer was slightly more potent than C16 fatty acid-$PEG_{24}$-PIE12-trimer (FIG. 4b).

These results demonstrate the successful application of modular multimer scaffold-based design to peptide drug optimization (both peptide geometry and localization to the site of action via conjugated membrane localizing cargoes). This approach allows for alterations in the scaffold to accommodate a variety of cargoes and chemistries (e.g., "click" chemistry), as well as rapid optimization of PEG linker lengths. For viruses that undergo membrane fusion within the endosome, such as Ebola, this strategy could be employed to attach an endosome-targeting moiety to localize an inhibitor to the site of virus entry and increase inhibitor potency. Additionally, the multimer scaffold allows for D-peptide conjugation to a variety of cargoes to modulate potency, pharmacokinetic properties (e.g., large branched PEGs, albumin, or albumin-binding peptides), and membrane localization.

Example 5

Effect of Membrane Localization on the Resistance Capacitor

Drug resistance is a constant threat to the effectiveness of HIV inhibitors. PIE12-trimer and its variants are an attractive drug candidates in part because of a strong resistance capacitor, which provides a high genetic barrier to resistance (Welch, 2010). The resistance capacitor depends on the diffusion-limited association rate for PIE12-trimer binding to gp41. The cholesterol and C16/18 alkane chain conjugation strategies described herein break through this kinetic barrier via inhibitor localization to viral entry sites (i.e., increasing effective inhibitor concentration and overcoming the diffusion rate limitation). In theory, this improvement in potency could come at the cost of weakening the resistance capacitor. To test for this possibility, the potency of chol- and C16/C18 alkane chain-conjugated PIE12-trimer was measured against previously identified resistance mutations (Welch, 2010).

Previous selection for resistance to PIE7-dimer (an earlier-generation D-peptide inhibitor) generated E560K/V570I, which minimally affects the potency of PIE12-trimer, but dramatically reduces PIE7-dimer potency. Selection of resistance to PIE12-trimer required more than a year of viral passaging, but ultimately resulted in the Q577R mutation, which decreases PIE12-trimer potency by >1000-fold (Welch, 2010). The effect of these resistance mutations on chol- and C16/18 alkane chain-PIE12-trimer potency is shown in Table 6. The relative effects of both resistance mutations are similar for PIE12-trimer and the cholesterol/alkane-conjugated PIE12-trimers. However, because of the greatly improved potency of the conjugated PIE12-trimers, these inhibitors maintain nM potency even against the severe Q577R resistance mutation. The impact of the less severe E560K/V570I resistance mutation is absorbed by all of the conjugated PIE12-trimers, as well as plain PIE12-trimer. These data suggest that the improvement in potency through C16/C18 alkane chain and cholesterol conjugation retains enough excess binding energy to maintain an effective resistance capacitor.

TABLE 6

Antiviral potency against resistant strains.

| | $IC_{50}$ (nM) | | |
|---|---|---|---|
| Inhibitor | WT HXB2 | E560K/V570I | Q577R |
| $PEG_4$-PIE12-trimer | 0.72 | 0.89 | >3 μM |
| Chol-$PEG_{24}$-PIE12-trimer | 0.013 | 0.01 | 10.1 |
| C8-$PEG_{24}$-PIE12-trimer | 0.42 | 0.86 | 452 |
| C16-$PEG_{24}$-PIE12-trimer | 0.09 | 0.045 | 39 |
| C18-$PEG_{24}$-PIE12-trimer | 0.054 | 0.035 | 32.5 |

Antiviral potency against identified resistant strains (HXB2 background). The $IC_{50}$ standard error of the mean values are <35% for all samples.

Example 6

Pharmacokinetic Properties of D-peptide Inhibitors

Although PIE12-trimers without a potency-enhancing cargo has desired antiviral properties, its relatively small size (~8 kD) may lead to a short serum half-life due to renal filtration. In addition to their potency-boosting effects, it was hypothesized that both cholesterol and alkyl conjugation will also lead to improvements in the pharmacokinetic (PK) properties, or pharmacokinetic enhancement, of these D-peptide inhibitors via interaction with cell membranes and albumin that slow renal clearance. Albumin serves as a carrier for both cholesterol and fatty acids, reducing the rate of renal filtration. Adherence to membrane surfaces may also slow the absorption of D-peptide inhibitor from the subcutaneous space, enabling prolonged dosing via a slow-release depot effect. This type of depot would be especially attractive for non-degradable D-peptides.

To evaluate the PK properties of the cholesterol conjugated D-peptides, the chol-PIE12-trimer and the PIE12-trimer were administered subcutaneously to rats (1 mg/kg). After subcutaneous administration, it was observed that the chol-PIE12-trimer with cholesterol conjugated with a $PEG_{24}$ linker shows an enhanced plasma half-life over the PIE12-trimer. More specifically, the chol-PIE12-trimer has a longer half-life of 3.7 hours compared to 2.7 hours for the PIE12-trimer. Furthermore, the chol-PIE12-trimer shows a reduced clearance of 24 mL/hour/kg compared to 572 mL/hr/kg for PIE12-trimer. As shown in FIG. 5, the chol-PIE12-trimer shows an improved concentration-time profile compared to the PIE12-trimer following subcutaneous administration in rats.

REFERENCES

1. Lu, M., Blacklow, S. C. & Kim, P. S. A trimeric structural domain of the HIV-1 transmembrane glycoprotein. *Nat Struct Biol* 2, 1075-82 (1995).
2. Chan, D. C., Fass, D., Berger, J. M. & Kim, P. S. Core structure of gp41 from the HIV envelope glycoprotein. *Cell* 89, 263-73 (1997).

3. Weissenhorn, W., Dessen, A., Harrison, S. C., Skehel, J. J. & Wiley, D. C. Atomic structure of the ectodomain from HIV-1 gp41. *Nature* 387, 426-30 (1997).
4. Tan, K., Liu, J., Wang, J., Shen, S. & Lu, M. Atomic structure of a thermostable subdomain of HIV-1 gp41. *Proc Natl Acad Sci USA* 94, 12303-8 (1997).
5. Wild, C., Oas, T., McDanal, C., Bolognesi, D. & Matthews, T. A synthetic peptide inhibitor of human immunodeficiency virus replication: correlation between solution structure and viral inhibition. *Proc Natl Acad Sci USA* 89, 10537-41 (1992).
6. Jiang, S., Lin, K., Strick, N. & Neurath, A. R. HIV-1 inhibition by a peptide. *Nature* 365, 113 (1993).
7. Eckert, D. M. & Kim, P. S. Mechanisms of viral membrane fusion and its inhibition. *Annu Rev Biochem* 70, 777-810 (2001).
8. Chan, D. C. & Kim, P. S. HIV entry and its inhibition. *Cell* 93, 681-4 (1998).
9. Furuta, R. A., Wild, C. T., Weng, Y. & Weiss, C. D. Capture of an early fusion-active conformation of HIV-1 gp41. *Nat Struct Biol* 5, 276-9 (1998).
10. Root, M. J. & Steger, H. K. HIV-1 gp41 as a target for viral entry inhibition. *Curr Pharm Des* 10, 1805-25 (2004).
11. Eckert, D. M., Malashkevich, V. N., Hong, L. H., Carr, P. A. & Kim, P. S. Inhibiting HIV-1 entry: discovery of D-peptide inhibitors that target the gp41 coiled-coil pocket. *Cell* 99, 103-15 (1999).
12. Root, M. J., Kay, M. S. & Kim, P. S. Protein design of an HIV-1 entry inhibitor. *Science* 291, 884-8 (2001).
13. Chan, D. C., Chutkowski, C. T. & Kim, P. S. Evidence that a prominent cavity in the coiled coil of HIV type 1 gp41 is an attractive drug target. *Proc Natl Acad Sci USA* 95, 15613-7 (1998).
14. Eckert, D. M. & Kim, P. S. Design of potent inhibitors of HIV-1 entry from the gp41 N-peptide region. *Proc Natl Acad Sci USA* 98, 11187-92 (2001).
15. Louis, J. M., Nesheiwat, I., Chang, L., Clore, G. M. & Bewley, C. A. Covalent trimers of the internal N-terminal trimeric coiled-coil of gp41 and antibodies directed against them are potent inhibitors of HIV envelope-mediated cell fusion. *J Biol Chem* 278, 20278-85 (2003).
16. Wild, C. T., Shugars, D. C., Greenwell, T. K., McDanal, C. B. & Matthews, T. J. Peptides corresponding to a predictive alpha-helical domain of human immunodeficiency virus type 1 gp41 are potent inhibitors of virus infection. Proc Natl Acad Sci USA 91, 9770-4 (1994).
17. Rimsky, L. T., Shugars, D. C. & Matthews, T. J. Determinants of human immunodeficiency virus type 1 resistance to gp41-derived inhibitory peptides. *J Virol* 72, 986-93 (1998).
18. Wei, X. et al. Emergence of resistant human immunodeficiency virus type 1 in patients receiving fusion inhibitor (T-20) monotherapy. *Antimicrob Agents Chemother* 46, 1896-905 (2002).
19. Milton, R. C., Milton, S. C. & Kent, S. B. Total chemical synthesis of a D-enzyme: the enantiomers of HIV-1 protease show reciprocal chiral substrate specificity. *Science* 256, 1445-8 (1992).
20. Sadowski, M. et al. A synthetic peptide blocking the apolipoprotein E/beta-amyloid binding mitigates beta-amyloid toxicity and fibril formation in vitro and reduces beta-amyloid plaques in transgenic mice. *Am J Pathol* 165, 937-48 (2004).
21. Pappenheimer, J. R., Dahl, C. E., Karnovsky, M. L. & Maggio, J. E. Intestinal absorption and excretion of octapeptides composed of D amino acids. *Proc Natl Acad Sci USA* 91, 1942-5 (1994).
22. Pappenheimer, J. R., Karnovsky, M. L. & Maggio, J. E. Absorption and excretion of undegradable peptides: role of lipid solubility and net charge. *J Pharmacol Exp Ther* 280, 292-300 (1997).
23. Schumacher, T. N. et al. Identification of D-peptide ligands through mirror-image phage display. *Science* 271, 1854-7 (1996).
24. Judice, J. K. et al. Inhibition of HIV type 1 infectivity by constrained alpha-helical peptides: implications for the viral fusion mechanism. *Proc Natl Acad Sci USA* 94, 13426-30 (1997).
25. Jin, B. S., Ryu, J. R., Ahn, K. & Yu, Y. G. Design of a peptide inhibitor that blocks the cell fusion mediated by glycoprotein 41 of human immunodeficiency virus type 1. *AIDS Res Hum Retroviruses* 16, 1797-804 (2000).
26. Sia, S. K., Carr, P. A., Cochran, A. G., Malashkevich, V. N. & Kim, P. S. Short constrained peptides that inhibit HIV-1 entry. *Proc Natl Acad Sci USA* 99, 14664-9 (2002).
27. Ernst, J. T. et al. Design of a protein surface antagonist based on alpha-helix mimicry: inhibition of gp41 assembly and viral fusion. *Angew Chem Int Ed Engl* 41, 278-81 (2002).
28. Stephens, O. M. et al. Inhibiting HIV fusion with a beta-peptide foldamer. *J Am Chem Soc* 127, 13126-7 (2005).
29. Debnath, A. K., Radigan, L. & Jiang, S. Structure-based identification of small molecule antiviral compounds targeted to the gp41 core structure of the human immunodeficiency virus type 1. *J Med Chem* 42, 3203-9 (1999).
30. Ferrer, M. et al. Selection of gp41-mediated HIV-1 cell entry inhibitors from biased combinatorial libraries of non-natural binding elements. *Nat Struct Biol* 6, 953-60 (1999).
31. Zhao, Q., Ernst, J. T., Hamilton, A. D., Debnath, A. K. & Jiang, S. XTT formazan widely used to detect cell viability inhibits HIV type 1 infection in vitro by targeting gp41. *AIDS Res Hum Retroviruses* 18, 989-97 (2002).
32. Jiang, S. et al. N-substituted pyrrole derivatives as novel human immunodeficiency virus type 1 entry inhibitors that interfere with the gp41 six-helix bundle formation and block virus fusion. *Antimicrob Agents Chemother* 48, 4349-59 (2004).
33. Frey, G. et al. Small molecules that bind the inner core of gp41 and inhibit HIV envelope-mediated fusion. *Proc Natl Acad Sci USA* 103, 13938-43 (2006).
34. Barbas, C. F. *Phage Display: A Laboratory Manual*, (Cold Springs Harbor Laboratory Press, New York, 2001).
35. Cole, J. L. & Garsky, V. M. Thermodynamics of peptide inhibitor binding to HIV-1 gp41. *Biochemistry* 40, 5633-41 (2001).
36. Harris, J. M. & Chess, R. B. Effect of pegylation on pharmaceuticals. *Nat Rev Drug Discov* 2, 214-21 (2003).
37. Steger, H. K. & Root, M. J. Kinetic dependence to HIV-1 entry inhibition. *J Biol Chem* 281, 25813-21 (2006).
38. Miller, M. D. et al. A human monoclonal antibody neutralizes diverse HIV-1 isolates by binding a critical gp41 epitope. *Proc Natl Acad Sci USA* 102, 14759-64 (2005).
39. Bianchi, E. et al. Covalent stabilization of coiled coils of the HIV gp41 N region yields extremely potent and broad inhibitors of viral infection. *Proc Natl Acad Sci USA* 102, 12903-8 (2005).

40. Platt, E. J., Durnin, J. P. & Kabat, D. Kinetic factors control efficiencies of cell entry, efficacies of entry inhibitors, and mechanisms of adaptation of human immunodeficiency virus. *J Virol* 79, 4347-56 (2005).
41. Choudhry, V. et al. Increased efficacy of HIV-1 neutralization by antibodies at low CCR5 surface concentration. *Biochem Biophys Res Commun* 348, 1107-15 (2006).
42. Chong, P., Sia, C., Tripet, B., James, O. & Klein, M. Comparative immunological properties of enantiomeric peptides *Letters in Peptide Science* 3, 99-106 (1996).
43. Hamburger, A. E., Kim, S., Welch, B. D. & Kay, M. S. Steric accessibility of the HIV-1 gp41 N-trimer region. *J Biol Chem* 280, 12567-72 (2005).
44. Otwinowski, Z. & Minor, W. Processing of X-ray diffraction data collected in oscillation mode. *Methods in Enzymology* 276, 307-326 (1997).
45. McCoy, A. J., Grosse-Kunstleve, R. W., Storoni, L. C. & Read, R. J. Likelihood-enhanced fast translation functions. *Acta Crystallogr D Biol Crystallogr* 61, 458-64 (2005).
46. CCP4 (Collaborative Computational Project, N. The CCP4 suite: programs for protein crystallography. *Acta Crystallogr D Biol Crystallogr* 50, 760-3 (1994).
47. Brunger, A. T. et al. Crystallography & NMR system: A new software suite for macromolecular structure determination. *Acta Crystallogr D Biol Crystallogr* 54, 905-21 (1998).
48. Emsley, P. & Cowtan, K. Coot: model-building tools for molecular graphics. *Acta Crystallogr D Biol Crystallogr* 60, 2126-32 (2004).
49. Noren, K. A. & Noren, C. J. Construction of high-complexity combinatorial phage display peptide libraries. *Methods* 23, 169-78 (2001).
50. Sidhu, S. S., Lowman, H. B., Cunningham, B. C. & Wells, J. A. Phage display for selection of novel binding peptides. *Methods Enzymol* 328, 333-63 (2000).
51. Welch, B. D., Francis, J. N., Redman, J. S., Paul, S., Weinstock, M. T., Reeves, J. D., Lie, Y. S., Whitby, F. G., Eckert, D. M., Hill, C. P., Root, M. J., and Kay, M. S. (2010) Design of a potent D-peptide HIV-1 entry inhibitor with a strong barrier to resistance. *J Virol* 84, 11235-44.
52. Welch, B. D., VanDemark, A. P., Heroux, A., Hill, C. P., and Kay, M. S. (2007) Potent D-peptide inhibitors of HIV-1 entry. *Proc Natl Acad Sci USA* 104, 16828-33.

What is claimed is:

1. A composition comprising at least three D-peptides and at least one potency-enhancing cargo molecule linked to a tetrameric scaffold, wherein:
   each D-peptide comprises the sequence of SEQ ID NO:37 (CDYPEWQWLC); and
   the potency-enhancing cargo molecule is a membrane localizing potency enhancing cargo molecule selected from the group consisting of a cholesterol or an analog thereof, alkane chain, and a fatty acid, and the membrane localizing potency-enhancing cargo molecule is linked to the tetrameric scaffold via a polyethylene glycol (PEG) linker comprising 12 to 132 PEG units.

2. The composition of claim 1, wherein the potency-enhancing cargo molecule is cholesterol or thiocholesterol.

3. The composition of claim 1, wherein the potency-enhancing cargo molecule is an alkane chain.

4. The composition of claim 3, wherein the potency-enhancing cargo molecule is a C8 alkane, a C16 alkane, or a C18 alkane.

5. The composition of claim 1, wherein the potency-enhancing cargo molecule is a fatty acid.

6. The composition of claim 5, wherein the potency-enhancing cargo molecule is a C8 fatty acid, a C16 fatty acid, or a C18 fatty acid.

7. The composition of claim 1, wherein each D-peptide is identical.

8. The composition of claim 1, wherein at least two D-peptides are different.

9. The composition of claim 1, wherein at least one D-peptide comprises the amino acid sequence of any one of SEQ ID NOS:6 and 23-29.

10. The composition of claim 1, wherein each D-peptide comprises an amino acid sequence of SEQ ID NO:26.

11. The composition of claim 1, wherein the tetrameric scaffold is a heterotetrameric scaffold comprising three NHS ester groups and a fourth orthogonal group, wherein the at least three D-peptides are linked to the heterotetrameric scaffold via the three NHS ester groups and the potency-enhancing cargo molecule is linked to the heterotetrameric scaffold via the fourth orthogonal group, wherein the fourth orthogonal group comprises the PEG linker comprising 12 to 132 PEG units.

12. The composition of claim 1, wherein the PEG linker is PEG12, PEG16, PEG24, PEG25, PEG26, PEG27, PEG28, PEG29, PEG30, PEG31, PEG32, PEG33, PEG34, PEG35, PEG36, PEG57 or PEG132.

13. The composition of claim 1, wherein the tetrameric scaffold comprises a tris, di-lysine, benzene ring, phosphate, or peptide core.

14. The composition of claim 11, wherein the potency enhancing cargo molecule is joined to the PEG linker via a reactive group.

15. The composition of claim 14, wherein the reactive group is a maleimide reactive group.

16. The composition of claim 11, wherein the tetrameric scaffold comprises a structure as follows:

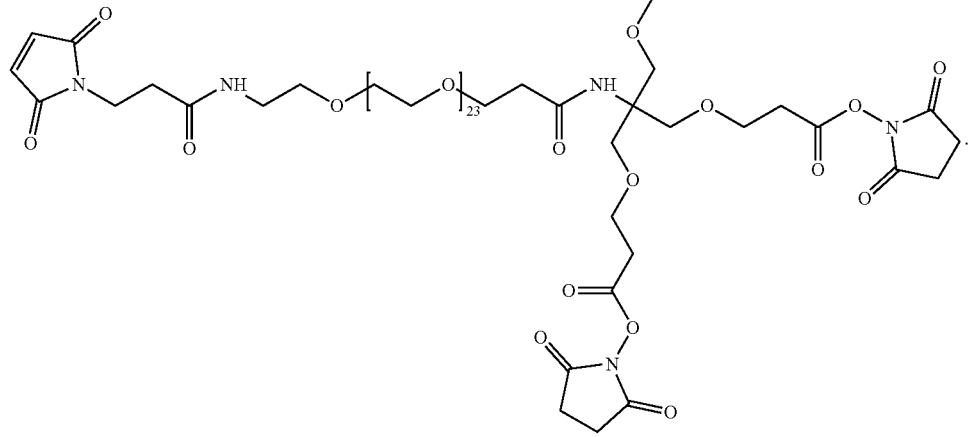

17. The composition of claim 1, wherein the composition inhibits HIV entry into a cell.

18. A pharmaceutical composition comprising the composition of claim 1 and a pharmaceutically acceptable carrier.

* * * * *

SEQUENCE LISTING

```
<160> NUMBER OF SEQ ID NOS: 37

<210> SEQ ID NO 1
<211> LENGTH: 18
<212> TYPE: PRT
<213> ORGANISM: Artificial Sequence
<220> FEATURE:
<223> OTHER INFORMATION: synthetic construct

<400> SEQUENCE: 1

Lys Lys Gly Ala Cys Glu Leu Leu Gly Trp Glu Trp Ala Trp Leu Cys
1               5                   10                  15

Ala Ala

<210> SEQ ID NO 2
<211> LENGTH: 16
<212> TYPE: PRT
<213> ORGANISM: Artificial Sequence
<220> FEATURE:
<223> OTHER INFORMATION: synthetic construct

<400> SEQUENCE: 2

Lys Lys Gly Ala Cys Glu Ser Pro Glu Trp Arg Trp Leu Cys Ala Ala
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic construct

<400> SEQUENCE: 3

Lys Lys Gly Ala Cys Asp Tyr Pro Glu Trp Arg Trp Leu Cys Ala Ala
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic construct
```

<400> SEQUENCE: 4

Lys Gly Ala Cys Asp Tyr Pro Glu Trp Arg Trp Leu Cys Ala Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic construct

<400> SEQUENCE: 5

Lys Gly Ala Cys Asp Tyr Pro Glu Trp Arg Trp Leu Cys Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic construct

<400> SEQUENCE: 6

Lys Gly Ala Cys Asp Tyr Pro Glu Trp Gln Trp Leu Cys Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic construct

<400> SEQUENCE: 7

Lys Gly Ala Cys Asp Tyr Lys Glu Trp Gln Trp Leu Cys Ala Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic construct

<400> SEQUENCE: 8

Lys Gly Ala Cys Asp Tyr Pro Glu Trp Gln Trp Leu Cys Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic construct

<400> SEQUENCE: 9

Lys Gly Ala Cys Asp Tyr Pro Glu Trp Gln Trp Leu Cys Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic construct

```
<400> SEQUENCE: 10

Lys Lys Gly Ala Cys Pro Arg Glu Trp His Trp Leu Cys Ala Ala
 1               5                  10                  15

<210> SEQ ID NO 11
<211> LENGTH: 13
<212> TYPE: PRT
<213> ORGANISM: Artificial Sequence
<220> FEATURE:
<223> OTHER INFORMATION: synthetic construct

<400> SEQUENCE: 11

Gly Ala Cys Pro Arg Glu Trp His Trp Leu Cys Ala Ala
 1               5                  10

<210> SEQ ID NO 12
<211> LENGTH: 16
<212> TYPE: PRT
<213> ORGANISM: Artificial Sequence
<220> FEATURE:
<223> OTHER INFORMATION: synthetic construct

<400> SEQUENCE: 12

Lys Lys Gly Ala Cys Asp Tyr Trp Glu Trp Arg Trp Leu Cys Ala Ala
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic construct

<400> SEQUENCE: 13

Asp Gly Ala Cys Asp Tyr Pro Glu Trp Arg Trp Leu Cys Ala Ala
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: synthetic construct

<400> SEQUENCE: 14

Lys Lys Gly Ala Cys Asp Asp Pro Asp Trp Gln Trp Leu Cys Ala Ala
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic construct

<400> SEQUENCE: 15

Lys Lys Gly Ala Cys Glu Asp Pro Asp Trp Gln Trp Leu Cys Ala Ala
 1               5                  10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic construct

<400> SEQUENCE: 16
```

```
Lys Lys Gly Ala Cys Glu Asp Pro Glu Trp Gln Trp Leu Cys Ala Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: synthetic construct

<400> SEQUENCE: 17

Lys Lys Gly Ala Cys Asn Asp Pro Glu Trp Gln Trp Leu Cys Ala Ala
1               5                   10                  15

<210> SEQ ID NO 18
<211> LENGTH: 18
<212> TYPE: PRT
<213> ORGANISM: Artificial Sequence
<220> FEATURE:
<223> OTHER INFORMATION: synthetic construct

<400> SEQUENCE: 18

Asp Gly Ala Cys Glu Ser Pro Glu Trp Gln Trp Leu Cys Ala Ala Gly
1               5                   10                  15

Ala Ala

<210> SEQ ID NO 19
<211> LENGTH: 15
<212> TYPE: PRT
<213> ORGANISM: Artificial Sequence
<220> FEATURE:
<223> OTHER INFORMATION: synthetic construct

<400> SEQUENCE: 19

Ala Cys Pro Pro Glu Trp His Trp Leu Cys Gly Gly Gly Ser Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: synthetic construct

<400> SEQUENCE: 20

Ala Cys Pro Val Glu Trp Arg Trp Leu Cys Gly Gly Gly Ser Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic construct

<400> SEQUENCE: 21

Ala Cys Pro Ile Glu Trp Arg Trp Leu Cys Gly Gly Gly Ser Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic construct
```

```
<400> SEQUENCE: 22

Ala Cys Pro Arg Glu Trp His Trp Leu Cys Gly Gly Gly Ser Ala
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: synthetic construct

<400> SEQUENCE: 23

Gly Ala Cys Asp Tyr Pro Glu Trp Gln Trp Leu Cys Ala Ala Gly Lys
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: synthetic construct

<400> SEQUENCE: 24

Gly Ala Cys Asp Tyr Pro Glu Trp Gln Trp Leu Cys Ala Ala Gly Lys
1               5                   10                  15

Lys

<210> SEQ ID NO 25
<211> LENGTH: 17
<212> TYPE: PRT
<213> ORGANISM: Artificial Sequence
<220> FEATURE:
<223> OTHER INFORMATION: synthetic construct

<400> SEQUENCE: 25

Lys Gly Ala Cys Asp Tyr Pro Glu Trp Gln Trp Leu Cys Ala Ala Gly
1               5                   10                  15

Lys

<210> SEQ ID NO 26
<211> LENGTH: 16
<212> TYPE: PRT
<213> ORGANISM: Artificial Sequence
<220> FEATURE:
<223> OTHER INFORMATION: synthetic construct

<400> SEQUENCE: 26

His Pro Cys Asp Tyr Pro Glu Trp Gln Trp Leu Cys Glu Leu Gly Lys
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: synthetic construct

<400> SEQUENCE: 27

His Pro Cys Asp Tyr Pro Glu Trp Gln Trp Leu Cys Lys Leu Gly Lys
1               5                   10                  15

<210> SEQ ID NO 28
<211> LENGTH: 16
<212> TYPE: PRT
<213> ORGANISM: Artificial Sequence
```

```
<220> FEATURE:
<223> OTHER INFORMATION: synthetic construct

<400> SEQUENCE: 28

His Pro Cys Asp Tyr Pro Glu Trp Gln Trp Leu Cys Arg Leu Gly Lys
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: synthetic construct

<400> SEQUENCE: 29

His Ala Cys Asp Tyr Pro Glu Trp Gln Trp Leu Cys Glu Leu Gly Lys
1               5                   10                  15

<210> SEQ ID NO 30
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (3)..(3)
<223> OTHER INFORMATION: Xaa = Any Amino Acid

<400> SEQUENCE: 30

Glu Trp Xaa Trp Leu
1               5

<210> SEQ ID NO 31
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (2)..(2)
<223> OTHER INFORMATION: Xaa = Any Amino Acid

<400> SEQUENCE: 31

Trp Xaa Trp Leu
1

<210> SEQ ID NO 32
<211> LENGTH: 5
<212> TYPE: PRT
<213> ORGANISM: Artificial Sequence
<220> FEATURE:
<223> OTHER INFORMATION: synthetic construct

<400> SEQUENCE: 32

Lys Lys Gly Ala Cys
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)...(10)
<223> OTHER INFORMATION: Xaa = Any Amino Acid
```

```
<400> SEQUENCE: 33

Cys Asp Tyr Xaa Glu Trp Xaa Trp Leu Cys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)...(12)
<223> OTHER INFORMATION: Xaa = Any Amino Acid

<400> SEQUENCE: 34

Cys Xaa Xaa Xaa Xaa Xaa Glu Trp Xaa Trp Leu Cys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)...(10)
<223> OTHER INFORMATION: Xaa = Any Amino Acid

<400> SEQUENCE: 35

Cys Xaa Xaa Xaa Glu Trp Xaa Trp Leu Cys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)...(10)
<223> OTHER INFORMATION: Xaa = Any Amino Acid

<400> SEQUENCE: 36

Cys Xaa Xaa Xaa Xaa Trp Xaa Trp Leu Cys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic construct

<400> SEQUENCE: 37

Cys Asp Tyr Pro Glu Trp Gln Trp Leu Cys
1               5                   10
```